US008071313B2

(12) United States Patent
Cucuzza et al.

(10) Patent No.: US 8,071,313 B2

(45) **Date of Patent: *Dec. 6, 2011**

(54) **PRIMERS AND PRIMER SETS FOR USE IN METHODS TO DETECT THE PRESENCE OF *ACIDOVORAX AVENAE* SUBSP. *CITRULLI***

(75) Inventors: James Cucuzza, Davis, CA (US); Carl Joseph Braun, III, Woodland, CA (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 896 days.

This patent is subject to a terminal disclaimer.

(21) Appl. No.: 11/987,735

(22) Filed: Dec. 4, 2007

(65) Prior Publication Data

US 2010/0280114 A1 Nov. 4, 2010

Related U.S. Application Data

(63) Continuation of application No. 10/630,573, filed on Jul. 30, 2003, now Pat. No. 7,319,005.

(60) Provisional application No. 60/400,305, filed on Aug. 1, 2002.

(51) Int. Cl.

*C12Q 1/68* (2006.01)
*C12P 19/34* (2006.01)
*C07H 21/04* (2006.01)

(52) U.S. Cl. ....... 435/6.15; 435/6.1; 435/6.12; 435/810; 536/24.32; 536/24.33

(58) Field of Classification Search ........................ None
See application file for complete search history.

(56) References Cited

U.S. PATENT DOCUMENTS

| | | | |
|---|---|---|---|
| 6,146,834 | A | 11/2000 | Schaad et al. |
| 6,423,499 | B1 | 7/2002 | Song et al. |
| 7,319,005 | B2 | 1/2008 | Cucuzza et al. |

FOREIGN PATENT DOCUMENTS

| | | | |
|---|---|---|---|
| WO | WO 9947706 | A1 * | 9/1999 |
| WO | WO 2004/013291 | A2 | 2/2004 |

OTHER PUBLICATIONS

Babadoost et al., “First Report of Bacterial Fruit Blotch of Watermelon Caused by *Acidovorax avenae* Subsp. *Citrulli* in Illinois”, Abstract, *Plant Disease* 86:443 (2002).

Buckner et al., “Melancholy Times for Watermelons,” *The Grower* 10-12 (1994).

Hopkins et al., “Bacterial Fruit Blotch of Watermelon,” 1994 Joint Technical Publication, University of Florida, University of Georgia, Clemson University, Purdue University, USA (1994).

Hopkins, “Wet Seed Treatments for the Control of Bacterial Fruit Blotch of Watermelon,” *Plant Disease* 80(5):529-532 (1996).

Hopkins, “Effect of Seed Contamination Level on Final Incidence of Bacterial Fruit Blotch of Direct-Seeded Watermelon,” Poster 1997 Annual Meeting of American Phytopathological Society, *Phytopathology* 87(6):S44 (1997).

Isakeit et al., “First Report of Infection of Honeydew with *Acidovorax avenae* subsp. *Citrulli,” Plant Disease*, 81(6):694 (1997).

Isakeit et al., “First Report of Infection of Honeydew with *Acidovorax avenae* subsp. *Citrulli*,” Abstract No. 3228, *Review of Plant Pathology*, 77(4):438 (1998).

Isakeit, “Bacterial Fruit Blotch of Watermelon,” *Texas Agricultural Extension Service, The Texas A&M University System* (1999).

O’Brien et al., “Bacterial blotch of melons caused by strains of *Acidovorax avenau* subsp. *citrulli*,” Abstract No. 289, *Review of Plant Pathology*, 79(1):38 (2000).

Pamphlet by Seminis Vegetable Seeds, Inc., “Bacterial Fruit Blotch of Melon” (2002).

International Search Report, International Application No. PCT/US03/24077 (published as WO 2004/013291 A3) (Aug. 2, 2004).

Rane et al., “Bacterial Fruit Blotch of Watermelon: Association of the Pathogen with Seed,” *Plant Disease*, 509-512 (1992).

Somodi et al., “Occurrence of a Bacterial Watermelon Fruit Blotch in Florida,” *Plant Disease*, 1052-1056 (1991).

Walcott et al., “Detection of *Acidovorax avenae* subsp. *citrulli* in watermelon seed using immunomagnetic separation and the polymerase chain reaction,” *Plant Disease*, 84(4):470-474 (2000).

Walcott et al., “Natural Outbreak of a Bacterial Fruit Rot of Cantaloupe in Georgia Caused by *Acidovorax avenae* subsp. *Citrulli*,” Abstract, *Plant Disease*, 84(3):372 (2000).

* cited by examiner

*Primary Examiner* — Diana Johannsen

(74) *Attorney, Agent, or Firm* — Alissa Eagle; Arnold & Porter LLP

(57) ABSTRACT

The present invention relates to oligonucleotide primers and primer sets that can be used to identify the bacterial pathogen *Acidovorax avenae* subsp. *citrulli* in a test sample.

28 Claims, 23 Drawing Sheets

FIG. 3a

Bacteria Fruit Blotch

Disease screen assay data sheet
WFB PCR #

Electrophoresis information

Gel Concentration: 2.0% Buffer: 0.5X TBE Amount of agarose used;
Volts: 97 Watts: 8 mAmps: 92 2.5g, 5.0g, (7.0g), other____
On: 1:45 Off: 3:15 Temp: RT (circle one)

Volume of DNA sample: 5μls Total reaction volume: 50μls

| Gel Lane | Aac Result | Xcv Result | Gel Lane | Aac Result | Xcv Result | Gel Lane | Aac Result | Xcv Result |
|---|---|---|---|---|---|---|---|---|
| 1. 1 Aac Rxns | - | | 37. 17 | + | | 73. 11 | | + |
| 2. 1 | - | | 38. 18 | + | | 74. 11 | | + |
| 3. 2 | - | | 39. 18 | + | | 75. 12 | | + |
| 4. 2 | - | | 40. 19 | - | | 76. 12 | | + |
| 5. 3 | - | | 41. 19 | - | | 77. 13 | | + |
| 6. 3 | - | | 42. 20 | + | | 78. 13 | | + |
| 7. 4 | - | | 43. 20 | + | | 79. 14 | | + |
| 8. 4 | - | | 44. $H_2O$ | - | | 80. 14 | | + |
| 9. 5 | - | | 45. $H_2O$ | - | | 81. 15 | | + |
| 10. 5 | - | | 46. TE | - | | 82. 15 | | + |
| 11. 6 | - | | 47. TE | - | | 83. 16 | | + |
| 12. 6 | - | | 48. DNA Hi | + | | 84. 16 | | + |
| 13. 7 | - | | 49. DNA Hi | + | | 85. Ladder | | |
| 14. 7 | - | | 50. DNA Low | + | | 86. N/A | | |
| 15. 8 | - | | 51. DNA Low | + | | 87. 17 | | + |
| 16. 8 | - | | 52. 1 | | + | 88. 17 | | + |
| 17. Ladder | | | 53. 1 | | + | 89. 18 | | + |
| 18. 9 | - | | 54. 2 | | + | 90. 18 | | + |
| 19. 9 | - | | 55. 2 | | + | 91. 19 | | + |
| 20. 10 | - | | 55. 3 | | + | 92. 19 | | + |
| 21. 10 | - | | 57. 3 | | + | 93. 20 | | - |
| 22. 11 | - | | 58. 4 | | + | 94. 20 | | - |
| 23. 11 | - | | 59. 4 | | + | 95. $H_2O$ | | - |
| 24. 12 | - | | 60. 5 | | + | 96. $H_2O$ | | - |
| 25. 12 | - | | 61. 5 | | + | 97. TE | | - |
| 26. 13 | - | | 62. 6 | | + | 98. TE | | - |
| 27. 13 | - | | 63. 6 | | + | 99. DNA Hi | | + |
| 28. 14 | - | | 64. 7 | | + | 100. DNA Hi | | + |
| 29. 14 | - | | 65. 7 | | + | 101. DNA Low | | + |
| 30. 15 | - | | 66. 8 | | + | 102. DNA Low | | + |
| 31. 15 | - | | 67. 8 | | + | 103. | | |
| 32. 16 | - | | 68. Ladder | | | 104. | | |
| 33. 16 | - | | 69. 9 | | + | 105. | | |
| 34. Ladder | | | 70. 9 | | + | 106. | | |
| 35. N/A | | | 71. 10 | | + | | | |
| 36. 17 | + | | 72. 10 | | + | | | |

Note: All samples are tested at a 1:50 dilution of the recovered (stock) DNA. NTC is a No Template Control

| Sample#'s | 1 & 2 | 3 & 4 | 5 & 6 | 7 & 8 | 9 & 10 | 11 & 12 | 13 & 14 | 15 & 16 | 17 & 18 |
|---|---|---|---|---|---|---|---|---|---|
| Positive | | | | | | | | | ✓ |
| Negative | ✓ | ✓ | ✓ | ✓ | ✓ | ✓ | ✓ | ✓ | |

FIG. 3b

BFB-PCR SEED HEALTH TESTING-50RXNS (20 SAMPLES)
PCR #: 975

ACIDOVORAX REACTIONS

XANTHOMONAS REACTIONS

|   | 1 | 2 | 3 | 4 | 5 | 6 | 7 | 8 | 9 | 10 | 11 | 12 |
|---|---|---|---|---|---|---|---|---|---|----|----|----|
| A | #1 | #1 | #9 | #9 | #17 | #17 | #1 | #1 | #9 | #9 | #17 | #17 |
| B | #2 | #2 | #10 | #10 | #18 | #18 | #2 | #2 | #10 | #10 | #18 | #18 |
| C | #3 | #3 | #11 | #11 | #19 SEED CONTROL | #19 SEED CONTROL | #3 | #3 | #11 | #11 | #19 SEED CONTROL | #19 SEED CONTROL |
| D | #4 | #4 | #12 | #12 | #20 SEED CONTROL | #20 SEED CONTROL | #4 | #4 | #12 | #12 | #20 SEED CONTROL | #20 SEED CONTROL |
| E | #5 | #5 | #13 | #13 | -H$_2$O CONTROL | -H$_2$O CONTROL | #5 | #5 | #13 | #13 | -H$_2$O CONTROL | -H$_2$O CONTROL |
| F | #6 | #6 | #14 | #14 | -TE CONTROL | -TE CONTROL | #6 | #6 | #14 | #14 | -TE CONTROL | -TE CONTROL |
| G | #7 | #7 | #15 | #15 | ⊕DNA CONTROL Aac | ⊕DNA CONTROL Aac | #7 | #7 | #15 | #15 | ⊕DNA CONTROL Aac | ⊕DNA CONTROL Aac |
| H | #8 | #8 | #16 | #16 | ⊕DNA CONTROL Aac | ⊕DNA CONTROL Aac | #8 | #8 | #16 | #16 | ⊕DNA CONTROL Aac | ⊕DNA CONTROL Aac |

FIG. 4a

Bacterial Fruit Blotch

Disease screen assay data sheet
WFB PCR # 980

Electrophoresis information

Gel Concentration: 2.0% Buffer: 0.5X TBE Amount of agarose used;
Volts: 98 Watts: 8 mAmps: 94 2.5g, 5.0g, (7.0g circled), other_____
On: 1:30 Off: 3:00 Temp: RT (circle one)

Volume of DNA sample: 5μls Total reaction volume: 50μls

| Gel Lane | Aac Result | Xcv Result | Gel Lane | Aac Result | Xcv Result | Gel Lane | Aac Result | Xcv Result |
|---|---|---|---|---|---|---|---|---|
| 1. 1 Aac Rxns | - | | 37. 17 | - | | 73. 11 | | + |
| 2. 1 | - | | 38. 18 | - | | 74. 11 | | + |
| 3. 2 | - | | 39. 18 | - | | 75. 12 | | + |
| 4. 2 | - | | 40. 19 | - | | 76. 12 | | + |
| 5. 3 | - | | 41. 19 | - | | 77. 13 | | + |
| 6. 3 | - | | 42. 20 | + | | 78. 13 | | + |
| 7. 4 | - | | 43. 20 | + | | 79. 14 | | + |
| 8. 4 | - | | 44. $H_2O$ | - | | 80. 14 | | + |
| 9. 5 | - | | 45. $H_2O$ | - | | 81. 15 | | + |
| 10. 5 | - | | 46. TE | - | | 82. 15 | | + |
| 11. 6 | - | | 47. TE | - | | 83. 16 | | + |
| 12. 6 | - | | 48. DNA Hi | + | | 84. 16 | | + |
| 13. 7 | - | | 49. DNA Hi | + | | 85. Ladder | | |
| 14. 7 | - | | 50. DNA Low | + | | 86. N/A | | |
| 15. 8 | - | | 51. DNA Low | + | | 87. 17 | | + |
| 16. 8 | - | | 52. 1 | | + | 88. 17 | | + |
| 17. Ladder | | | 53. 1 | | + | 89. 18 | | + |
| 18. 9 | - | | 54. 2 | | + | 90. 18 | | + |
| 19. 9 | - | | 55. 2 | | + | 91. 19 | | + |
| 20. 10 | - | | 55. 3 | | + | 92. 19 | | + |
| 21. 10 | - | | 57. 3 | | + | 93. 20 | | - |
| 22. 11 | - | | 58. 4 | | + | 94. 20 | | - |
| 23. 11 | - | | 59. 4 | | + | 95. $H_2O$ | | - |
| 24. 12 | - | | 60. 5 | | - | 96. $H_2O$ | | - |
| 25. 12 | - | | 61. 5 | | - | 97. TE | | - |
| 26. 13 | - | | 62. 6 | | + | 98. TE | | - |
| 27. 13 | - | | 63. 6 | | + | 99. DNA Hi | | + |
| 28. 14 | - | | 64. 7 | | + | 100. DNA Hi | | + |
| 29. 14 | - | | 65. 7 | | + | 101. DNA Low | | + |
| 30. 15 | - | | 66. 8 | | + | 102. DNA Low | | + |
| 31. 15 | - | | 67. 8 | | + | 103. | | |
| 32. 16 | - | | 68. Ladder | | | 104. | | |
| 33. 16 | - | | 69. 9 | | + | 105. | | |
| 34. Ladder | | | 70. 9 | | + | 106. | | |
| 35. N/A | | | 71. 10 | | + | | | |
| 36. 17 | - | | 72. 10 | | + | | | |

Note: All samples are tested at a 1:50 dilution of the recovered (stock) DNA. NTC is a No Template Control

| Sample#'s | 1 & 2 | 3 & 4 | 5 & 6 | 7 & 8 | 9 & 10 | 11 & 12 | 13 & 14 | 15 & 16 | 17 & 18 |
|---|---|---|---|---|---|---|---|---|---|
| Positive | | | | | | | | | |
| Negative | ✓ | ✓ | ✓ | ✓ | ✓ | ✓ | ✓ | ✓ | ✓ |

FIG. 4b

BFB-PCR SEED HEALTH TESTING-50RXNS (20 SAMPLES)

PCR #: 980

ACIDOVORAX REACTIONS XANTHOMONAS REACTIONS

| | 1 | 2 | 3 | 4 | 5 | 6 | 7 | 8 | 9 | 10 | 11 | 12 |
|---|---|---|---|---|---|---|---|---|---|---|---|---|
| A | #1 | #1 | #9 | #9 | #17 | #17 | #1 | #1 | #9 | #9 | #17 | #17 |
| B | #2 | #2 | #10 | #10 | #18 | #18 | #2 | #2 | #10 | #10 | #18 | #18 |
| C | #3 | #3 | #11 | #11 | #19 SEED CONTROL | #19 SEED CONTROL | #3 | #3 | #11 | #11 | #19 SEED CONTROL | #19 SEED CONTROL |
| D | #4 | #4 | #12 | #12 | #20 SEED CONTROL | #20 SEED CONTROL | #4 | #4 | #12 | #12 | #20 SEED CONTROL | #20 SEED CONTROL |
| E | #5 | #5 | #13 | #13 | -$H_2O$ CONTROL | -$H_2O$ CONTROL | #5 | #5 | #13 | #13 | -$H_2O$ CONTROL | -$H_2O$ CONTROL |
| F | #6 | #6 | #14 | #14 | -TE CONTROL | -TE CONTROL | #6 | #6 | #14 | #14 | -TE CONTROL | -TE CONTROL |
| G | #7 | #7 | #15 | #15 | ⊕DNA CONTROL Aac | ⊕DNA CONTROL Aac | #7 | #7 | #15 | #15 | ⊕DNA CONTROL Xcv | ⊕DNA CONTROL Xcv |
| H | #8 | #8 | #16 | #16 | ⊕DNA CONTROL Aac | ⊕DNA CONTROL Aac | #8 | #8 | #16 | #16 | ⊕DNA CONTROL Xcv | ⊕DNA CONTROL Xcv |

FIG. 5a

Bacterial Fruit Blotch

Disease screen assay data sheet
WFB PCR # 981

Electrophoresis information
Gel Concentration: 2.0% Buffer: 0.5X TBE Amount of agarose used;
Volts: 98 Watts: 9 mAmps: 92 2.5g, 5.0g, (7.0g), other_____
On: 1:30 Off: 3:00 Temp: RT (circle one)

Volume of DNA sample: 5µls Total reaction volume: 50µls

| Gel Lane | Aac Result | Xcv Result | Gel Lane | Aac Result | Xcv Result | Gel Lane | Aac Result | Xcv Result |
|---|---|---|---|---|---|---|---|---|
| 1. 1 Aac Rxns | - | | 37. 17 | - | | 73. 11 | | + |
| 2. 1 | - | | 38. 18 | - | | 74. 11 | | + |
| 3. 2 | - | | 39. 18 | - | | 75. 12 | | + |
| 4. 2 | - | | 40. 19 | - | | 76. 12 | | + |
| 5. 3 | - | | 41. 19 | - | | 77. 13 | | + |
| 6. 3 | - | | 42. 20 | + | | 78. 13 | | - |
| 7. 4 | - | | 43. 20 | + | | 79. 14 | | - |
| 8. 4 | - | | 44. $H_2O$ | - | | 80. 14 | | + |
| 9. 5 | - | | 45. $H_2O$ | - | | 81. 15 | | + |
| 10. 5 | - | | 46. TE | - | | 82. 15 | | + |
| 11. 6 | - | | 47. TE | - | | 83. 16 | | + |
| 12. 6 | - | | 48. DNA Hi | + | | 84. 16 | | + |
| 13. 7 | - | | 49. DNA Hi | + | | 85. Ladder | | |
| 14. 7 | - | | 50. DNA Low | + | | 86. N/A | | |
| 15. 8 | - | | 51. DNA Low | + | | 87. 17 | | + |
| 16. 8 | - | | 52. 1 | | + | 88. 17 | | + |
| 17. Ladder | | | 53. 1 | | + | 89. 18 | | + |
| 18. 9 | - | | 54. 2 | | + | 90. 18 | | + |
| 19. 9 | - | | 55. 2 | | + | 91. 19 | | + |
| 20. 10 | - | | 55. 3 | | + | 92. 19 | | + |
| 21. 10 | - | | 57. 3 | | + | 93. 20 | | - |
| 22. 11 | - | | 58. 4 | | + | 94. 20 | | - |
| 23. 11 | - | | 59. 4 | | + | 95. $H_2O$ | | - |
| 24. 12 | - | | 60. 5 | | + | 96. $H_2O$ | | - |
| 25. 12 | - | | 61. 5 | | + | 97. TE | | - |
| 26. 13 | - | | 62. 6 | | + | 98. TE | | - |
| 27. 13 | - | | 63. 6 | | + | 99. DNA Hi | | + |
| 28. 14 | - | | 64. 7 | | + | 100. DNA Hi | | + |
| 29. 14 | - | | 65. 7 | | + | 101. DNA Low | | + |
| 30. 15 | - | | 66. 8 | | + | 102. DNA Low | | + |
| 31. 15 | - | | 67. 8 | | + | 103. | | |
| 32. 16 | - | | 68. Ladder | | | 104. | | |
| 33. 16 | - | | 69. 9 | | + | 105. | | |
| 34. Ladder | | | 70. 9 | | + | 106. | | |
| 35. N/A | | | 71. 10 | | + | | | |
| 36. 17 | - | | 72. 10 | | + | | | |

Note: All samples are tested at a 1:50 dilution of the recovered (stock) DNA. NTC is a No Template Control

| Sample#'s | 1 & 2 | 3 & 4 | 5 & 6 | 7 & 8 | 9 & 10 | 11 & 12 | 13 & 14 | 15 & 16 | 17 & 18 |
|---|---|---|---|---|---|---|---|---|---|
| Positive | | | | | | | | | |
| Negative | ✓ | ✓ | ✓ | ✓ | ✓ | ✓ | ✓ | ✓ | ✓ |

FIG. 5b

BFB-PCR SEED HEALTH TESTING-50RXNS (20 SAMPLES)

PCR #: 981

ACIDOVORAX REACTIONS | XANTHOMONAS REACTIONS

| | 1 | 2 | 3 | 4 | 5 | 6 | 7 | 8 | 9 | 10 | 11 | 12 |
|---|---|---|---|---|---|---|---|---|---|---|---|---|
| A | #1 | #1 | #9 | #9 | #17 | #17 | #1 | #1 | #9 | #9 | #17 | #17 |
| B | #2 | #2 | #10 | #10 | #18 | #18 | #2 | #2 | #10 | #10 | #18 | #18 |
| C | #3 | #3 | #11 | #11 | #19 SEED CONTROL | #19 SEED CONTROL | #3 | #3 | #11 | #11 | #19 SEED CONTROL | #19 SEED CONTROL |
| D | #4 | #4 | #12 | #12 | #20 SEED CONTROL | #20 SEED CONTROL | #4 | #4 | #12 | #12 | #20 SEED CONTROL | #20 SEED CONTROL |
| E | #5 | #5 | #13 | #13 | $-H_2O$ CONTROL | $-H_2O$ CONTROL | #5 | #5 | #13 | #13 | $-H_2O$ CONTROL | $-H_2O$ CONTROL |
| F | #6 | #6 | #14 | #14 | -TE CONTROL | -TE CONTROL | #6 | #6 | #14 | #14 | -TE CONTROL | -TE CONTROL |
| G | #7 | #7 | #15 | #15 | ⊕DNA CONTROL Aac | ⊕DNA CONTROL Aac | #7 | #7 | #15 | #15 | ⊕DNA CONTROL Aac | ⊕DNA CONTROL Aac |
| H | #8 | #8 | #16 | #16 | ⊕DNA CONTROL Aac | ⊕DNA CONTROL Aac | #8 | #8 | #16 | #16 | ⊕DNA CONTROL Aac | ⊕DNA CONTROL Aac |

FIG. 6a

Bacterial Fruit Blotch

Disease screen assay data sheet
WFB PCR # 984

Electrophoresis information

Gel Concentration: 2.0% Buffer: 0.5X TBE Amount of agarose used;
Volts: 100 Watts: 8 mAmps: 98 2.5g, 5.0g, (7.0g), other_____
On: 1:15 Off: 2:45 Temp: RT (circle one)

Volume of DNA sample: 5µls Total reaction volume: 50µls

| Gel Lane | Aac Result | Xcv Result | Gel Lane | Aac Result | Xcv Result | Gel Lane | Aac Result | Xcv Result |
|---|---|---|---|---|---|---|---|---|
| 1. 1 Aac Rxns | - | | 37. 17 | - | | 73. 11 | | + |
| 2. 1 | - | | 38. 18 | - | | 74. 11 | | + |
| 3. 2 | - | | 39. 18 | - | | 75. 12 | | + |
| 4. 2 | - | | 40. 19 | - | | 76. 12 | | + |
| 5. 3 | - | | 41. 19 | - | | 77. 13 | | + |
| 6. 3 | - | | 42. 20 | + | | 78. 13 | | + |
| 7. 4 | - | | 43. 20 | + | | 79. 14 | | + |
| 8. 4 | - | | 44. $H_2O$ | - | | 80. 14 | | + |
| 9. 5 | - | | 45. $H_2O$ | - | | 81. 15 | | + |
| 10. 5 | - | | 46. TE | - | | 82. 15 | | + |
| 11. 6 | + | | 47. TE | - | | 83. 16 | | + |
| 12. 6 | - | | 48. DNA Hi | + | | 84. 16 | | + |
| 13. 7 | - | | 49. DNA Hi | + | | 85. Ladder | | |
| 14. 7 | + | | 50. DNA Low | + | | 86. N/A | | |
| 15. 8 | - | | 51. DNA Low | + | | 87. 17 | | + |
| 16. 8 | + | | 52. 1 | | + | 88. 17 | | + |
| 17. Ladder | | | 53. 1 | | + | 89. 18 | | + |
| 18. 9 | - | | 54. 2 | | + | 90. 18 | | + |
| 19. 9 | - | | 55. 2 | | + | 91. 19 | | + |
| 20. 10 | - | | 55. 3 | | + | 92. 19 | | + |
| 21. 10 | - | | 57. 3 | | + | 93. 20 | | - |
| 22. 11 | - | | 58. 4 | | + | 94. 20 | | - |
| 23. 11 | - | | 59. 4 | | + | 95. $H_2O$ | | - |
| 24. 12 | - | | 60. 5 | | + | 96. $H_2O$ | | - |
| 25. 12 | - | | 61. 5 | | + | 97. TE | | - |
| 26. 13 | - | | 62. 6 | | + | 98. TE | | - |
| 27. 13 | - | | 63. 6 | | + | 99. DNA Hi | | + |
| 28. 14 | + | | 64. 7 | | + | 100. DNA Hi | | + |
| 29. 14 | + | | 65. 7 | | + | 101. DNA Low | | + |
| 30. 15 | + | | 66. 8 | | + | 102. DNA Low | | + |
| 31. 15 | + | | 67. 8 | | + | 103. | | |
| 32. 16 | - | | 68. Ladder | | | 104. | | |
| 33. 16 | - | | 69. 9 | | + | 105. | | |
| 34. Ladder | | | 70. 9 | | + | 106. | | |
| 35. N/A | | | 71. 10 | | + | | | |
| 36. 17 | - | | 72. 10 | | + | | | |

Note: All samples are tested at a 1:50 dilution of the recovered (stock) DNA. NTC is a No Template Control

| Sample#'s | 1 & 2 | 3 & 4 | 5 & 6 | 7 & 8 | 9 & 10 | 11 & 12 | 13 & 14 | 15 & 16 | 17 & 18 |
|---|---|---|---|---|---|---|---|---|---|
| Positive | | | ✓ | ✓ | | | ✓ | ✓ | |
| Negative | ✓ | ✓ | | | ✓ | ✓ | | | ✓ |

FIG. 6b

BFB-PCR SEED HEALTH TESTING-50RXNS (20 SAMPLES)

PCR #: 984

ACIDOVORAX REACTIONS

XANTHOMONAS REACTIONS

| | 1 | 2 | 3 | 4 | 5 | 6 | 7 | 8 | 9 | 10 | 11 | 12 |
|---|---|---|---|---|---|---|---|---|---|---|---|---|
| A | #1 | #1 | #9 | #9 | #17 | #17 | #1 | #1 | #9 | #9 | #17 | #17 |
| B | #2 | #2 | #10 | #10 | #18 | #18 | #2 | #2 | #10 | #10 | #18 | #18 |
| C | #3 | #3 | #11 | #11 | #19 SEED CONTROL | #19 SEED CONTROL | #3 | #3 | #11 | #11 | #19 SEED CONTROL | #19 SEED CONTROL |
| D | #4 | #4 | #12 | #12 | #20 SEED CONTROL | #20 SEED CONTROL | #4 | #4 | #12 | #12 | #20 SEED CONTROL | #20 SEED CONTROL |
| E | #5 | #5 | #13 | #13 | -$H_2O$ CONTROL | -$H_2O$ CONTROL | #5 | #5 | #13 | #13 | -$H_2O$ CONTROL | -$H_2O$ CONTROL |
| F | #6 | #6 | #14 | #14 | -TE CONTROL | -TE CONTROL | #6 | #6 | #14 | #14 | -TE CONTROL | -TE CONTROL |
| G | #7 | #7 | #15 | #15 | ⊕DNA CONTROL Aac | ⊕DNA CONTROL Aac | #7 | #7 | #15 | #15 | ⊕DNA CONTROL Aac | ⊕DNA CONTROL Aac |
| H | #8 | #8 | #16 | #16 | ⊕DNA CONTROL Aac | ⊕DNA CONTROL Aac | #8 | #8 | #16 | #16 | ⊕DNA CONTROL Aac | ⊕DNA CONTROL Aac |

FIG. 7a

Bacterial Fruit Blotch

Disease screen assay data sheet

WFB PCR # 987

Electrophoresis information

Gel Concentration: 2.0% Buffer: 0.5X TBE Amount of agarose used; 2.5g, 5.0g, (7.0g), other____ (circle one)

Volts: 100 Watts: 9 mAmps: 98

On: 2:00 Off: 3:30 Temp: RT

Volume of DNA sample: 5μls Total reaction volume: 50μls

| Gel Lane | Aac Result | Xcv Result | Gel Lane | Aac Result | Xcv Result | Gel Lane | Aac Result | Xcv Result |
|---|---|---|---|---|---|---|---|---|
| 1. 1 Aac Rxns | - | | 37. 17 | + | | 73. 11 | | + |
| 2. 1 | - | | 38. 18 | + | | 74. 11 | | + |
| 3. 2 | - | | 39. 18 | + | | 75. 12 | | + |
| 4. 2 | - | | 40. 19 | - | | 76. 12 | | + |
| 5. 3 | + | | 41. 19 | - | | 77. 13 | | + |
| 6. 3 | + | | 42. 20 | + | | 78. 13 | | + |
| 7. 4 | + | | 43. 20 | + | | 79. 14 | | + |
| 8. 4 | + | | 44. $H_2O$ | - | | 80. 14 | | + |
| 9. 5 | + | | 45. $H_2O$ | - | | 81. 15 | | + |
| 10. 5 | + | | 46. TE | - | | 82. 15 | | + |
| 11. 6 | + | | 47. TE | - | | 83. 16 | | + |
| 12. 6 | + | | 48. DNA Hi | + | | 84. 16 | | + |
| 13. 7 | - | | 49. DNA Hi | + | | 85. Ladder | | |
| 14. 7 | - | | 50. DNA Low | + | | 86. N/A | | |
| 15. 8 | - | | 51. DNA Low | + | | 87. 17 | | + |
| 16. 8 | - | | 52. 1 | | + | 88. 17 | | + |
| 17. Ladder | | | 53. 1 | | + | 89. 18 | | + |
| 18. 9 | - | | 54. 2 | | + | 90. 18 | | + |
| 19. 9 | - | | 55. 2 | | + | 91. 19 | | + |
| 20. 10 | - | | 55. 3 | | + | 92. 19 | | + |
| 21. 10 | - | | 57. 3 | | + | 93. 20 | | - |
| 22. 11 | + | | 58. 4 | | + | 94. 20 | | - |
| 23. 11 | + | | 59. 4 | | + | 95. $H_2O$ | | - |
| 24. 12 | - | | 60. 5 | | + | 96. $H_2O$ | | - |
| 25. 12 | - | | 61. 5 | | + | 97. TE | | - |
| 26. 13 | - | | 62. 6 | | + | 98. TE | | - |
| 27. 13 | - | | 63. 6 | | + | 99. DNA Hi | | + |
| 28. 14 | - | | 64. 7 | | + | 100. DNA Hi | | + |
| 29. 14 | - | | 65. 7 | | + | 101. DNA Low | | + |
| 30. 15 | + | | 66. 8 | | + | 102. DNA Low | | + |
| 31. 15 | + | | 67. 8 | | + | 103. | | |
| 32. 16 | + | | 68. Ladder | | | 104. | | |
| 33. 16 | + | | 69. 9 | | + | 105. | | |
| 34. Ladder | | | 70. 9 | | + | 106. | | |
| 35. N/A | | | 71. 10 | | + | | | |
| 36. 17 | + | | 72. 10 | | + | | | |

Note: All samples are tested at a 1:50 dilution of the recovered (stock) DNA. NTC is a No Template Control

| Sample#'s | 1 & 2 | 3 & 4 | 5 & 6 | 7 & 8 | 9 & 10 | 11 & 12 | 13 & 14 | 15 & 16 | 17 & 18 |
|---|---|---|---|---|---|---|---|---|---|
| Positive | | ✓ | ✓ | | | ✓ | | ✓ | ✓ |
| Negative | ✓ | | | ✓ | ✓ | | ✓ | | |

FIG. 7b

BFB-PCR SEED HEALTH TESTING-50RXNS (20 SAMPLES)

PCR #: 984

ACIDOVORAX REACTIONS

XANTHOMONAS REACTIONS

| | 1 | 2 | 3 | 4 | 5 | 6 | 7 | 8 | 9 | 10 | 11 | 12 |
|---|---|---|---|---|---|---|---|---|---|---|---|---|
| A | #1 | #1 | #9 | #9 | #17 | #17 | #1 | #1 | #9 | #9 | #17 | #17 |
| B | #2 | #2 | #10 | #10 | #18 | #18 | #2 | #2 | #10 | #10 | #18 | #18 |
| C | #3 | #3 | #11 | #11 | #19 SEED CONTROL | #19 SEED CONTROL | #3 | #3 | #11 | #11 | #19 SEED CONTROL | #19 SEED CONTROL |
| D | #4 | #4 | #12 | #12 | #20 SEED CONTROL | #20 SEED CONTROL | #4 | #4 | #12 | #12 | #20 SEED CONTROL | #20 SEED CONTROL |
| E | #5 | #5 | #13 | #13 | $-H_2O$ CONTROL | $-H_2O$ CONTROL | #5 | #5 | #13 | #13 | $-H_2O$ CONTROL | $-H_2O$ CONTROL |
| F | #6 | #6 | #14 | #14 | -TE CONTROL | -TE CONTROL | #6 | #6 | #14 | #14 | -TE CONTROL | -TE CONTROL |
| G | #7 | #7 | #15 | #15 | ⊕DNA CONTROL Aac | ⊕DNA CONTROL Aac | #7 | #7 | #15 | #15 | ⊕DNA CONTROL Xcv | ⊕DNA CONTROL Xcv |
| H | #8 | #8 | #16 | #16 | ⊕DNA CONTROL Aac | ⊕DNA CONTROL Aac | #8 | #8 | #16 | #16 | ⊕DNA CONTROL Xcv | ⊕DNA CONTROL Xcv |

FIG. 8a

Bacterial Fruit Blotch

Disease screen assay data sheet
WFB PCR # 993

Electrophoresis information
Gel Concentration: 2.0% Buffer: 0.5X TBE Amount of agarose used;
Volts: 130 Watts: 15 mAmps: 117 2.5g, 5.0g, 7.0g, other 12g/600ml
On: 1:40 Off: 3:00 Temp: RT (circle one) Run gel together with PCR #99

Volume of DNA sample: 5μls Total reaction volume: 50μls

| Gel Lane | Aac Result | Xcv Result | Gel Lane | Aac Result | Xcv Result | Gel Lane | Aac Result | Xcv Result |
|---|---|---|---|---|---|---|---|---|
| 1. 1 Aac Rxns | + | | 37. 17 | - | | 73. 11 | | + |
| 2. 1 | + | | 38. 18 | - | | 74. 11 | | + |
| 3. 2 | + | | 39. 18 | - | | 75. 12 | | + |
| 4. 2 | + | | 40. 19 | - | | 76. 12 | | + |
| 5. 3 | - | | 41. 19 | - | | 77. 13 | | + |
| 6. 3 | - | | 42. 20 | + | | 78. 13 | | + |
| 7. 4 | + | | 43. 20 | + | | 79. 14 | | + |
| 8. 4 | + | | 44. $H_2O$ | - | | 80. 14 | | + |
| 9. 5 | + | | 45. $H_2O$ | - | | 81. 15 | | + |
| 10. 5 | - | | | | | 82. 15 | | + |
| 11. 6 | + | | 46. TE | - | | 83. 16 | | + |
| 12. 6 | + | | 47. TE | - | | 84. 16 | | + |
| 13. 7 | + | | 48. DNA Hi | + | | 85. Ladder | | |
| 14. 7 | + | | 49. DNA Hi | + | | 86. N/A | | |
| 15. 8 | - | | 50. DNA Low | + | | 87. 17 | | + |
| 16. 8 | + | | 51. DNA Low | + | | 88. 17 | | + |
| 17. Ladder | | | 52. 1 | | + | 89. 18 | | + |
| 18. 9 | - | | 53. 1 | | + | 90. 18 | | + |
| 19. 9 | - | | 54. 2 | | + | 91. 19 | | + |
| 20. 10 | - | | 55. 2 | | + | 92. 19 | | + |
| 21. 10 | - | | 55. 3 | | + | 93. 20 | | - |
| 22. 11 | - | | 57. 3 | | + | 94. 20 | | - |
| 23. 11 | - | | 58. 4 | | + | 95. $H_2O$ | | - |
| 24. 12 | - | | 59. 4 | | + | | | |
| 25. 12 | - | | 60. 5 | | + | 96. $H_2O$ | | - |
| 26. 13 | - | | 61. 5 | | + | | | |
| 27. 13 | - | | 62. 6 | | + | 97. TE | | - |
| 28. 14 | - | | 63. 6 | | + | 98. TE | | - |
| 29. 14 | - | | 64. 7 | | + | 99. DNA Hi | | + |
| 30. 15 | - | | 65. 7 | | + | 100. DNA Hi | | + |
| 31. 15 | - | | 66. 8 | | + | 101. DNA Low | | + |
| 32. 16 | - | | 67. 8 | | + | 102. DNA Low | | + |
| 33. 16 | - | | 68. Ladder | | | 103. | | |
| 34. Ladder | | | 69. 9 | | + | 104. | | |
| 35. N/A | | | 70. 9 | | + | 105. | | |
| 36. 17 | - | | 71. 10 | | + | 106. | | |
| | | | 72. 10 | | + | | | |

Note: All samples are tested at a 1:50 dilution of the recovered (stock) DNA. NTC is a No Template Control

| Sample#'s | 1 & 2 | 3 & 4 | 5 & 6 | 7 & 8 | 9 & 10 | 11 & 12 | 13 & 14 | 15 & 16 | 17 & 18 |
|---|---|---|---|---|---|---|---|---|---|
| Positive | ✓ | ✓ | ✓ | ✓ | | | | | |
| Negative | | | | | ✓ | ✓ | ✓ | ✓ | ✓ |

FIG. 8b

BFB-PCR SEED HEALTH TESTING-50RXNS (20 SAMPLES)

PCR #: 993

ACIDOVORAX REACTIONS | XANTHOMONAS REACTIONS

| | 1 | 2 | 3 | 4 | 5 | 6 | 7 | 8 | 9 | 10 | 11 | 12 |
|---|---|---|---|---|---|---|---|---|---|---|---|---|
| A | #1 | #1 | #9 | #9 | #17 | #17 | #1 | #1 | #9 | #9 | #17 | #17 |
| B | #2 | #2 | #10 | #10 | #18 | #18 | #2 | #2 | #10 | #10 | #18 | #18 |
| C | #3 | #3 | #11 | #11 | #19 SEED CONTROL | #19 SEED CONTROL | #3 | #3 | #11 | #11 | #19 SEED CONTROL | #19 SEED CONTROL |
| D | #4 | #4 | #12 | #12 | #20 SEED CONTROL | #20 SEED CONTROL | #4 | #4 | #12 | #12 | #20 SEED CONTROL | #20 SEED CONTROL |
| E | #5 | #5 | #13 | #13 | $-H_2O$ CONTROL | $-H_2O$ CONTROL | #5 | #5 | #13 | #13 | $-H_2O$ CONTROL | $-H_2O$ CONTROL |
| F | #6 | #6 | #14 | #14 | -TE CONTROL | -TE CONTROL | #6 | #6 | #14 | #14 | -TE CONTROL | -TE CONTROL |
| G | #7 | #7 | #15 | #15 | ⊕DNA CONTROL Aac | ⊕DNA CONTROL Aac | #7 | #7 | #15 | #15 | ⊕DNA CONTROL Xcv | ⊕DNA CONTROL Xcv |
| H | #8 | #8 | #16 | #16 | ⊕DNA CONTROL Aac | ⊕DNA CONTROL Aac | #8 | #8 | #16 | #16 | ⊕DNA CONTROL Xcv | ⊕DNA CONTROL Xcv |

FIG. 9a

Bacterial Fruit Blotch

Disease screen assay data sheet
WFB PCR # 976

Electrophoresis information

Gel Concentration: 2.0% Buffer: 0.5X TBE Amount of agarose used;
Volts: 98 Watts: 8 mAmps: 92 2.5g, 5.0g, (7.0g), other____
On: 1:30 Off: 3:00 Temp: RT (circle one)

Volume of DNA sample: 5μls Total reaction volume: 50μls

| Gel Lane | Aac Result | Xcv Result | Gel Lane | Aac Result | Xcv Result | Gel Lane | Aac Result | Xcv Result |
|---|---|---|---|---|---|---|---|---|
| 1. 1 Aac Rxns | - | | 37. 17 | - | | 73. 11 | | + |
| 2. 1 | - | | 38. 18 | - | | 74. 11 | | + |
| 3. 2 | - | | 39. 18 | - | | 75. 12 | | + |
| 4. 2 | - | | 40. 19 | - | | 76. 12 | | + |
| 5. 3 | - | | 41. 19 | - | | 77. 13 | | + |
| 6. 3 | - | | 42. 20 | + | | 78. 13 | | + |
| 7. 4 | - | | 43. 20 | + | | 79. 14 | | + |
| 8. 4 | - | | 44. $H_2O$ | - | | 80. 14 | | + |
| 9. 5 | - | | 45. $H_2O$ | - | | 81. 15 | | + |
| 10. 5 | - | | | | | 82. 15 | | + |
| 11. 6 | - | | 46. TE | - | | 83. 16 | | + |
| 12. 6 | - | | 47. TE | - | | 84. 16 | | + |
| 13. 7 | - | | 48. DNA Hi | + | | 85. Ladder | | |
| 14. 7 | - | | 49. DNA Hi | + | | 86. N/A | | |
| 15. 8 | - | | 50. DNA Low | + | | 87. 17 | | + |
| 16. 8 | - | | 51. DNA Low | + | | 88. 17 | | + |
| 17. Ladder | | | 52. 1 | | + | 89. 18 | | + |
| 18. 9 | - | | 53. 1 | | + | 90. 18 | | + |
| 19. 9 | - | | 54. 2 | | + | 91. 19 | | + |
| 20. 10 | - | | 55. 2 | | + | 92. 19 | | + |
| 21. 10 | - | | 55. 3 | | + | 93. 20 | | - |
| 22. 11 | - | | 57. 3 | | + | 94. 20 | | - |
| 23. 11 | - | | 58. 4 | | + | 95. $H_2O$ | | - |
| 24. 12 | - | | 59. 4 | | + | 96. $H_2O$ | | - |
| 25. 12 | - | | 60. 5 | | + | | | |
| 26. 13 | - | | 61. 5 | | + | 97. TE | | - |
| 27. 13 | - | | 62. 6 | | + | 98. TE | | - |
| 28. 14 | - | | 63. 6 | | + | 99. DNA Hi | | + |
| 29. 14 | - | | 64. 7 | | + | 100. DNA Hi | | + |
| 30. 15 | - | | 65. 7 | | + | 101. DNA Low | | + |
| 31. 15 | - | | 66. 8 | | + | 102. DNA Low | | + |
| 32. 16 | - | | 67. 8 | | + | 103. | | |
| 33. 16 | - | | 68. Ladder | | | 104. | | |
| 34. Ladder | | | 69. 9 | | + | 105. | | |
| 35. N/A | | | 70. 9 | | + | 106. | | |
| 36. 17 | - | | 71. 10 | | + | | | |
| | | | 72. 10 | | + | | | |

Note: All samples are tested at a 1:50 dilution of the recovered (stock) DNA. NTC is a No Template Control

| Sample#'s | 1 & 2 | 3 & 4 | 5 & 6 | 7 & 8 | 9 & 10 | 11 & 12 | 13 & 14 | 15 & 16 | 17 & 18 |
|---|---|---|---|---|---|---|---|---|---|
| Positive | | | | | | | | | |
| Negative | ✓ | ✓ | ✓ | ✓ | ✓ | ✓ | ✓ | ✓ | ✓ |

BFB-PCR SEED HEALTH TESTING-50RXNS (20 SAMPLES)

PCR #: 976

FIG. 9b

ACIDOVORAX REACTIONS | XANTHOMONAS REACTIONS

| | 1 | 2 | 3 | 4 | 5 | 6 | 7 | 8 | 9 | 10 | 11 | 12 |
|---|---|---|---|---|---|---|---|---|---|---|---|---|
| A | #1 | #1 | #9 | #9 | #17 | #17 | #1 | #1 | #9 | #9 | #17 | #17 |
| B | #2 | #2 | #10 | #10 | #18 | #18 | #2 | #2 | #10 | #10 | #18 | #18 |
| C | #3 | #3 | #11 | #11 | #19 SEED CONTROL | #19 SEED CONTROL | #3 | #3 | #11 | #11 | #19 SEED CONTROL | #19 SEED CONTROL |
| D | #4 | #4 | #12 | #12 | #20 SEED CONTROL | #20 SEED CONTROL | #4 | #4 | #12 | #12 | #20 SEED CONTROL | #20 SEED CONTROL |
| E | #5 | #5 | #13 | #13 | -$H_2O$ CONTROL | -$H_2O$ CONTROL | #5 | #5 | #13 | #13 | -$H_2O$ CONTROL | -$H_2O$ CONTROL |
| F | #6 | #6 | #14 | #14 | -TE CONTROL | -TE CONTROL | #6 | #6 | #14 | #14 | -TE CONTROL | -TE CONTROL |
| G | #7 | #7 | #15 | #15 | ⊕DNA CONTROL Aac | ⊕DNA CONTROL Aac | #7 | #7 | #15 | #15 | ⊕DNA CONTROL Aac | ⊕DNA CONTROL Aac |
| H | #8 | #8 | #16 | #16 | ⊕DNA CONTROL Aac | ⊕DNA CONTROL Aac | #8 | #8 | #16 | #16 | ⊕DNA CONTROL Aac | ⊕DNA CONTROL Aac |

PRIMERS AND PRIMER SETS FOR USE IN METHODS TO DETECT THE PRESENCE OF *ACIDOVORAX AVENAE* SUBSP. *CITRULLI*

RELATED APPLICATION INFORMATION

This application is a continuation of U.S. patent application Ser. No. 10/630,573 filed on Jul. 30, 2003, now U.S. Pat. No. 7,319,005, which claims the benefit of U.S. Provisional Application No. 60/400,305 filed on Aug. 1, 2002, both of which applications are hereby incorporated by reference.

FIELD OF THE INVENTION

The present invention relates to molecular biology, specifically, oligonucleotide primer sequences that can be used in amplification methods, such as PCR and BIO-PCR, to identify the bacterial fruit blotch pathogen, *Acidovorax avenae* subsp. *citrulli* in a test sample.

BACKGROUND OF THE INVENTION

Bacterial fruit blotch (also known as watermelon fruit blotch) is a serious disease that strikes cotyledons, leaves and young fruit of cucurbits particularly, watermelon and cantaloupe. Bacterial fruit blotch is caused by the bacterium, *Acidovorax avenae* subsp. *citrulli*. Fruit is susceptible to infection during flowering and fruit set and infection does not spread via contact during fruit transit or storage.

Symptoms of the bacterial fruit blotch appear on the fruit shortly before harvest, which is often long after the period of infection. Infected areas (lesions) on the rind of watermelon fruit appear water-soaked or oily. Cracks sometimes develop in the more advanced lesions that may contain brown, gummy ooze. Such cracks allow other organisms to enter and cause fruit decay. In melons, the external symptoms on fruit can be very limited, however, the causal agent is invasive and can cause serious degradation of the fruit flesh.

Symptoms can also occur on the foliage. The earliest symptoms are water-soaking between the veins on the underside of the seedling cotyledons (seed leaves) (Thomas Isakeit, "Bacterial Fruit Blotch of Watermelon," L-5222, Texas Agricultural Extension Service, The Texas A& M University System, 6/99). These areas eventually dry up and die. Id. On true leaves, the disease can form distinctive brown, elongated lesions on and next to the veins, which can also appear water-soaked. Id. The bacteria also produce brown, circular spots on the leaves although, similar lesions can be caused by a number of other agents. Id. Nonetheless, the large lesions on fruit and angular lesions on the true leaves are distinctive for bacterial fruit blotch. Id.

The bacterial fruit blotch pathogen typically spreads to areas where it has not occurred before via seed (seed borne). Environmental conditions play a key role in symptom development and disease severity. Id. Rain helps spread bacteria onto developing fruit. Overhead irrigation also contributes to disease development. High temperatures (higher than 90° F.) and high humidity are also a factor.

Infection of commercial melon fields with bacterial fruit blotch during the 1990's has, in extreme cases, caused losses of about 90% of growers' fields. Such losses have been devastating to the industry. Therefore, there is a need in the industry for sensitive methods of identifying bacterial fruit blotch in seed lots prior to planting to insure against the presence, contamination and spread of the disease in the field.

SUMMARY OF THE INVENTION

The present invention relates to oligonucleotide primers comprising sequences of 5'-CGCGCCGACCGAGACCTG-3' (SEQ. ID NO:1) and 5'-GGGGCACGCCAACATCCT-3' (SEQ. ID NO:2).

The present invention also relates to a primer set comprising the polynucleotide sequence of 5'-CGCGCCGACCGAGACCTG-3' (SEQ. ID NO:1) and 5'-GGGGCACGCCAACATCCT-3' (SEQ. ID NO:2).

The present invention further relates to a method of detecting the presence of *Acidovorax avenae* subsp. *citrulli*. in a test sample. The method involves the steps of: (1) providing DNA from a test sample suspected of containing DNA of *Acidovorax avenae* subsp. *citrulli* or a test sample of bacterial cells or microorganisms suspected of containing DNA of *Acidovorax avenae* subsp. *citrulli*; (2) amplifying a target sequence of DNA from the test sample using a primer set comprising a polynucleotide sequence of: 5'-CGCGCCGACCGAGACCTG-3' (SEQ. ID NO:1) and 5'-GGGGCACGCCAACATCCT-3' (SEQ. ID NO:2) under amplification conditions; and (3) detecting the presence of the amplification product(s) of the target sequence of DNA as an indication of the presence of *Acidovorax avenae* subsp. *citrulli* in the test sample.

The present invention further relates to a method of evaluating or monitoring the efficacy of treatments utilized to eliminate *Acidovorax avenae* subsp. *citrulli* from a seed lot. The method involves the steps of: (1) providing a first test sample from a seed lot suspected of containing DNA of *Acidovorax avenae* subsp. *citrulli*; (2) providing DNA from said first test sample or bacterial cells or microorganisms from the first test sample suspected of containing *Acidovorax avenae* subsp. *citrulli*; (3) amplifying a target sequence of DNA using a primer set comprising: 5'-CGCGCCGACCGAGACCTG-3' (SEQ. ID NO:1) and 5'-GGGGCACGCCAACATCCT-3' (SEQ. ID NO:2) under amplification conditions; (4) detecting the presence of amplification products of the target DNA as an indication of the presence of *Acidovorax avenae* subsp. *citrulli* in the first test sample; (5) treating the seed lot from which the first test sample was obtained or a portion thereof with a composition to reduce or eradicate *Acidovorax avenae* subsp. *citrulli*; (6) providing a second test sample from the treated seed lot or treated portion thereof; (7) providing DNA from said second test sample or bacterial cells or microorganisms from the second test sample suspected of containing *Acidovorax avenae* subsp. *citrulli*; (8) amplifying target DNA using a primer set comprising: 5'-CGCGCCGACCGAGACCTG-3' (SEQ. ID NO:1) and 5'-GGGGCACGCCAACATCCT-3' (SEQ. ID NO:2) under amplification conditions; (9) detecting the presence of the amplification product(s) of the target DNA as an indication of the presence of *Acidovorax avenae* subsp. *citrulli* in the second test sample; and (10) comparing the amount of amplification product(s) or absence of amplification products in the second test sample to the amount of amplification products detected in the first test sample in step (4) as an indication of whether or not the treatment has been successful in reducing or eradicating *Acidovorax avenae* subsp. *citrulli* in the seed lot.

The present invention further relates to a test kit for identifying *Acidovorax avenae* subsp. *citrulli*. The test kit comprises at least one primer set comprising the sequence of: CGCGCCGACCGAGACCTG-3' (SEQ. ID NO:1) and 5'-GGGGCACGCCAACATCCT-3' (SEQ. ID NO:2).

The present invention further relates to a test kit for identifying *Acidovorax avenae* subsp. *citrulli*. The test kit comprises a primer set comprising oligonucleotides having the sequence of 5'-CGCGCCGACCGAGACCTG-3' (SEQ. ID NO:1) and 5'-GGGGCACGCCAACATCCT-3' (SEQ. ID NO:2).

BRIEF DESCRIPTION OF THE FIGURES

FIG. 3*a*-3*c* shows the results of PCR testing for BFB using the primers of the present invention. Specifically, FIGS. 3*a* and 3*c* show the results of the gel electrophoresis of the amplification products from the PCR. FIG. 3*b* shows the PCR assay sheet used during the procedure.

FIG. 4*a*-4*c* shows the results of PCR testing for BFB using the primers of the present invention. Specifically, FIGS. 4*a* and 4*c* show the results of the gel electrophoresis of the amplification products from the PCR. FIG. 4*b* shows the PCR assay sheet used during the procedure.

FIG. 5*a*-5*c* shows the results of PCR testing for BFB using the primers of the present invention. Specifically, FIGS. 5*a* and 5*c* show the results of the gel electrophoresis of the amplification products from the PCR. FIG. 5*b* shows the PCR assay sheet used during the procedure.

FIG. 6*a*-6*c* shows the results of PCR testing for BFB using the primers of the present invention. Specifically, FIGS. 6*a* and 6*c* show the results of the gel electrophoresis of the amplification products from the PCR. FIG. 6*b* shows the PCR assay sheet used during the procedure.

FIG. 7*a*-7*c* shows the results of PCR testing for BFB using the primers of the present invention. Specifically, FIGS. 7*a* and 7*c* show the results of the gel electrophoresis of the amplification products from the PCR. FIG. 7*b* shows the PCR assay sheet used during the procedure.

FIG. 8*a*-8*c* shows the results of PCR testing for BFB using the primers of the present invention. Specifically, FIGS. 8*a* and 8*c* show the results of the gel electrophoresis of the amplification products from the PCR. FIG. 8*b* shows the PCR assay sheet used during the procedure.

FIG. 9*a*-9*c* shows the results of PCR testing for BFB using the primers of the present invention. Specifically, FIGS. 9*a* and 9*c* show the results of the gel electrophoresis of the amplification products from the PCR. FIG. 9*b* shows the PCR assay sheet used during the procedure.

SEQUENCE LISTING

Figure 1:
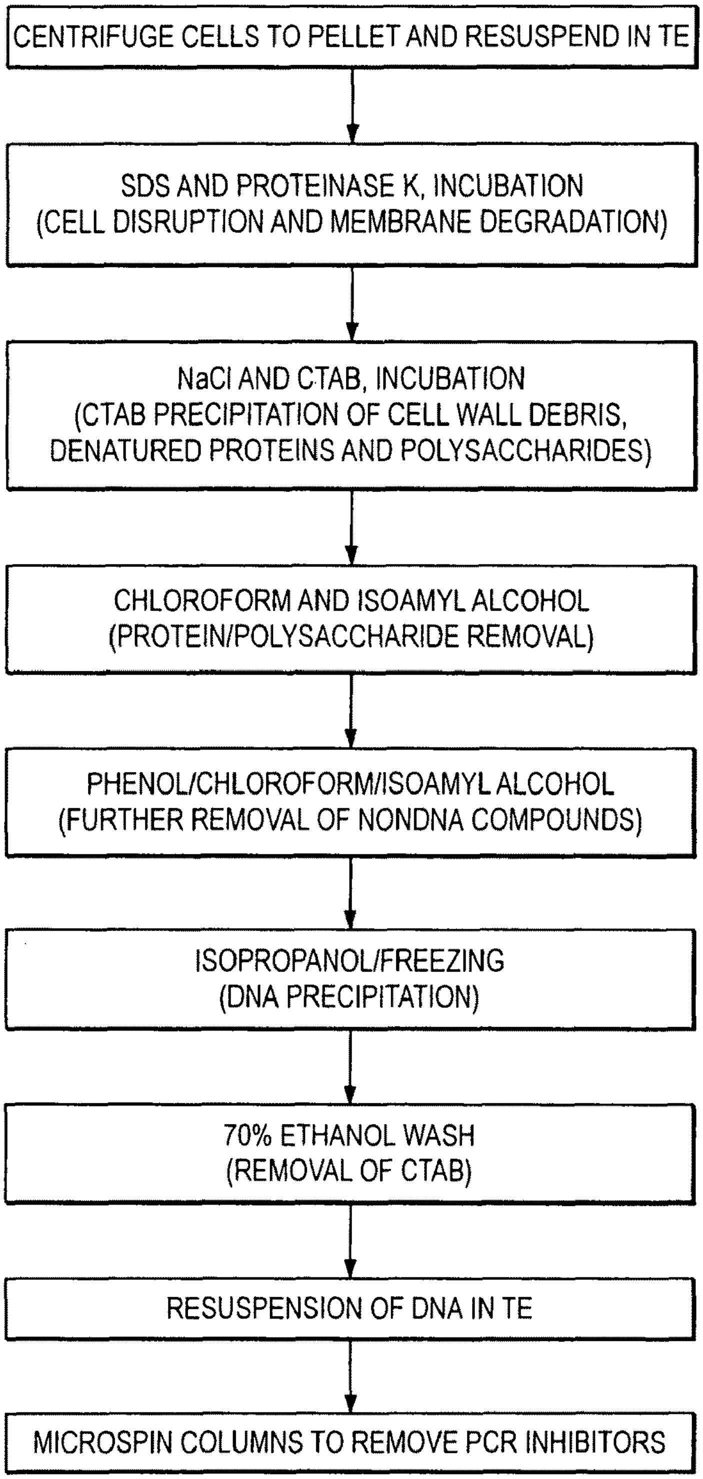
FIG. 1 is a chart of a DNA Extraction Process-Post Seedwash.
Figure 2:
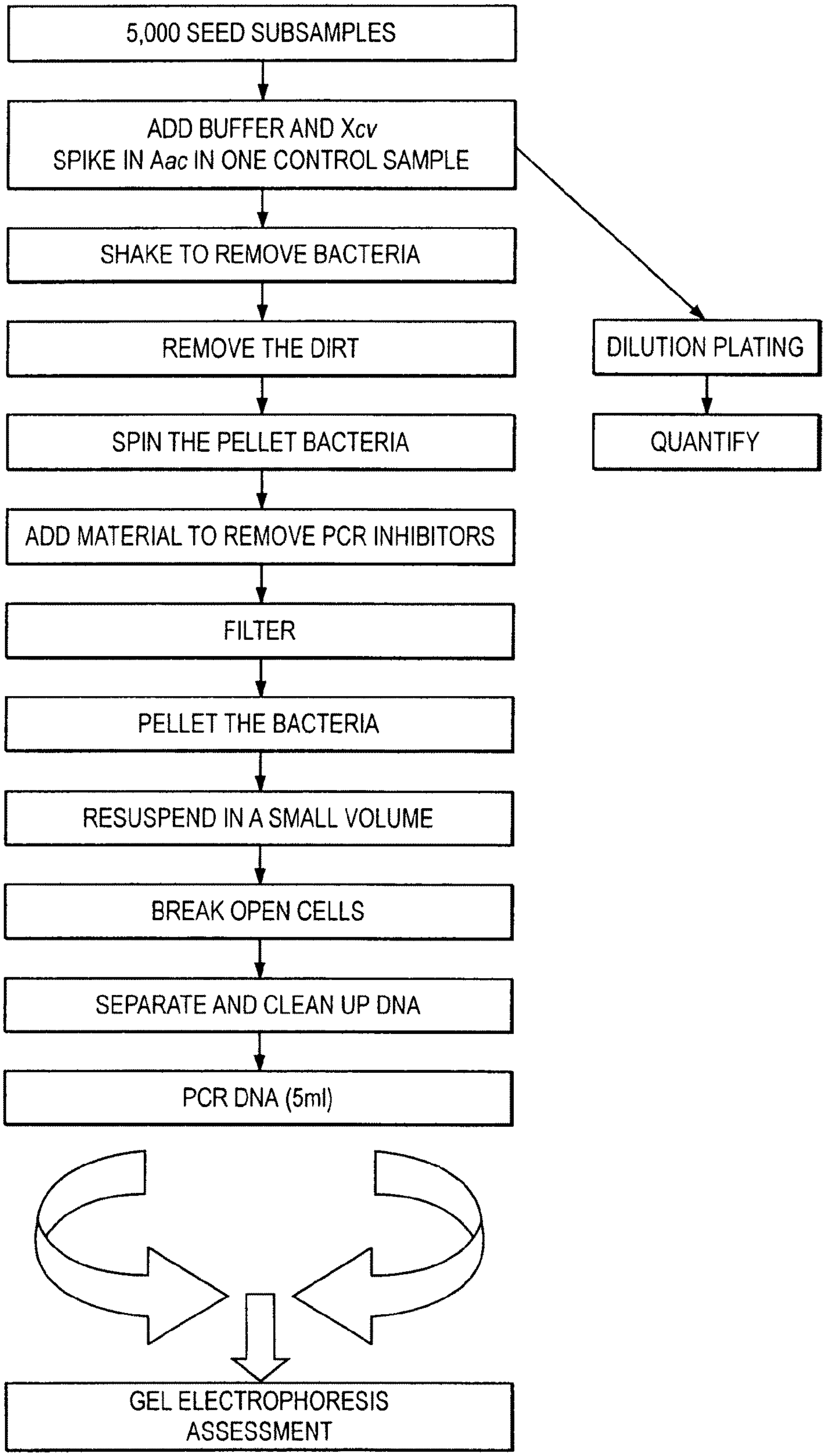
FIG. 2 is a chart of Bacterial Fruit Blotch (BFB) Polymerase Chain Reaction (PCR) Assay for Watermelon Seedlots.

The present application also contains three (3) polynucleotide sequences. The base pairs in these sequences are represented by the following base codes:

| Symbol | Meaning |
|---|---|
| A | Adenine |
| C | Cytosine |
| G | Guanine |
| T | Thymine |
| U | Uracil |
| N | A or C or G or T/U |

DEFINITIONS

As used herein, the term "amplification conditions" refers to those conditions that promote annealing and extension of one or more polynucleotide sequences. It is well known in the art that such annealing is dependent in a rather predictable manner on several parameters, including temperature, ionic strength, sequence length, complementarity, and G:C content. For example, lowering the temperature in the environment of complementary polynucleotide sequences promotes annealing. For any given set of polynucleotide sequences, melt temperature, or $T_m$, can be estimated by any of several known methods. Typically, diagnostic applications utilize hybridization temperatures which are close to (i.e. within 10° C.) the melt temperature. Ionic strength or "salt" concentration also impacts the melt temperature, since small cations tend to stabilize the formation of duplexes. Typical salt concentrations depend on the nature and valency of the cation but are readily understood by those skilled in the art. Similarly, high GC content and increased sequence length are also known to stabilize duplex formation because G:C pairings involve 3 hydrogen bonds where A:T pairs have just two, and because longer sequences have more hydrogen bonds holding the sequences together. Thus, high GC content and longer sequence lengths impact the hybridization conditions by elevating the melt temperature.

Once sequences are selected for a given diagnostic application, the G:C content and length will be known and can be accounted for in determining precisely what hybridization conditions will encompass. Since ionic strength is typically optimized for enzymatic activity, the only parameter left to vary is the temperature. Generally, the hybridization temperature is selected close to or at the $T_m$ of the primers or probe. Thus, obtaining suitable hybridization conditions for a particular primer/probe set is well within ordinary skill of one practicing this art.

The terms "oligonucleotide" and "primer" are used interchangeably herein.

The term "test sample" refers to bacterial cells, microorganisms or extracted DNA. The test sample can be a sample suspected of containing bacterial cells or microorganisms and thus, the DNA of bacterial cells or microorganisms, or a test sample containing extracted DNA.

As used herein, the term "polynucleotide" refers to a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, either by methylation and/or by capping, and unmodified forms of the polynucleotide.

As used herein, the term "primer" refers to a polynucleotide that is approximately between about fifteen (15) to twenty-five (25) nucleotides in length. A primer is capable of acting as a point of initiation of synthesis on a polynucleotide sequence when placed under appropriate conditions. The primer will be completely or substantially complementary to a region of the target polynucleotide sequence to be copied. Therefore, under conditions conducive to hybridization, the primer will anneal to the complementary region of the target sequence. Upon addition of suitable reactants, including, but not limited to, a polymerase, nucleotide triphosphates, etc., the primer is extended by the polymerizing agent to form a copy of the target sequence. The primer may be single-stranded or alternatively may be partially double-stranded.

As used herein, the term "probe" refers to a polynucleotide that is at least eight (8) nucleotides in length and which forms a hybrid structure with a target sequence, due to complementarity of at least one sequence in the probe with a sequence in the target region. The polynucleotide regions of the probe can be composed of DNA and/or RNA and/or synthetic nucleotide analogs. Preferably, the probe does not contain a sequence complementary to the sequence(s) used to prime for a target sequence during the polymerase chain reaction.

As used herein, the term "label" or "labeled" refers to any atom or moiety which can be used to provide a detectable (preferably, quantifiable) signal, and which can be attached to a polynucleotide, primer or probe. A wide variety of labels and conjugation techniques, including direct and indirect labeling, are known and are reported extensively in both the scientific and patent literature.

Examples of labels that can be used include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241.

As used herein, the term "plant" includes plant cells, plant protoplasts, plant cell tissue cultures from which cucurbitaceae plants can be regenerated, plant calli, plant cell clumps, and plant cells that are intact in plants, or parts of plants, such as embryos, pollen, ovules, flowers, leaves, seeds, roots, root tips and the like.

DETAILED DESCRIPTION OF THE INVENTION

In one embodiment, the present invention provides novel oligonucleotide primers and primer sets. These primer and primer sets described herein can be used in amplification methods (such as polymerase chain reaction and BIO-PCR) and packaged into kits for use in amplification methods for the purpose of detecting *Acidovorax avenae* subsp. *citrulli* in a test sample. Additionally, these primers and primer sets can be used in amplification methods (such as polymerase chain reaction and BIO-PCR) to evaluate or monitor the efficacy of treatments being used to eliminate *Acidovorax avenae* subsp. *citrulli* from a seed lot. These oligonucleotide primers are designated as SEQ. ID NO:1 and SEQ ID NO:2 and their polynucleotide sequences are as follows: (1) (forward) 5'-CGCGCCGACCGAGACCTG-3' (SEQ. ID NO:1); and (2) (reverse) 5'-GGGGCACGCCAACATCCT-3' (SEQ. ID NO:2). When the primers designated in SEQ ID NO:1 and SEQ ID NO:2 are used in PCR, an amplification product of approximately 232 base pairs is obtained for *Acidovorax avenae* subsp. *citrulli.*

The primers of the present invention can be prepared using techniques known in the art, including, but not limited to, cloning and digestion of the appropriate sequences and direct chemical synthesis. Unlike other primers known in the art, the primers of the present invention are sensitive in detecting the presence of *Acidovorax avenae* subsp. *citrulli* (Aac) in a test sample. For example, the primers of the present invention can identify the presence of *Acidovorax avenae* subsp. *citrulli* in a single seed in a sample of about 5,000 seeds.

Chemical synthesis methods that can be used to make the primers of the present invention, include, but are not limited to, the phosphotriester method described by Narang et al., *Methods in Enzymology,* 68:90 (1979), the phosphodiester method disclosed by Brown et al., *Methods in Enzymology,* 68:109 (1979), the diethylphosphoramidate method disclosed by Beaucage et al., *Tetrahedron Letters,* 22:1859 (1981) and the solid support method described in U.S. Pat. No. 4,458,066. The use of an automated oligonucleotide synthesizer to prepare synthetic oligonucleotide primers of the present invention is also contemplated herein. Additionally, if desired, the primers can be labeled using techniques known in the art.

As mentioned briefly earlier, the oligonucleotide primers and primer sets of the present invention can be used in an amplification method to identify the bacterial pathogen *Acidovorax avenae* subsp. *citrulli*. Additionally, these primers and primer sets can be used in amplification methods (such as polymerase chain reaction and BIO-PCR) to evaluate or monitor the efficacy of treatments being used to eliminate *Acidovorax avenae* subsp. *citrulli* from a seed lot. The amplification methods that can be used include polymerase chain reaction (PCR), which is described in U.S. Pat. Nos. 4,683,195 and 4,683,202, or BIO-PCR which is described in U.S. Pat. No. 6,410,223 and Schaad et al., *Phytopath.,* 85:243-248 (1995).

Generally, in PCR, a target polynucleotide sequence is amplified by reaction with at least one oligonucleotide primer or pair of oligonucleotide primers. The primer(s) hybridize to a complementary region of the target sequence and a DNA polymerase extends the primer(s) to amplify the target sequence. If the PCR test is designed properly, a DNA fragment of one size dominates the reaction products (the target polynucleotide sequence which is the amplification product). The amplification cycle is repeated to increase the concentration of the single target polynucleotide sequence. The amplification products can be separated using methods known in the art such as gel electrophoresis. Southern blot analysis or blot analysis can be used to verify that the amplification product is in fact the target polynucleotide sequence. Alternatively, a far more stringent way to verify the product is to sequence it.

Alternative methods of conducting PCR with various combinations of primers (i.e. from 1 to 3 primers) are known in the art and are described in Maniatis, *Molecular Cloning: A Laboratory Manual*, Cold Spring Harbor, N.Y. (1989). These methods include asymmetric PCR, PCR using mismatched or degenerate primers, reverse transcriptase PCR, arbitrarily primed PCR (Welsh et al., *Nucleic Acids Res.* 18:7213-7218 (1990)), RAPD PCR, IMS-PCR (Islam et al., *J. Clin. Micro.,* 30:2801-2806 (1992); and multiwell PCR. Additionally, amplification methods using a single primer, such as described by Judd et al., *Appl. Env. Microbiol.,* 59:1702-1708 (1993) are also contemplated herein.

BIO-PCR combines biological preamplification of the PCR target organism with enzymatic amplification of the PCR target. The advantages of BIO-PCR over the standard PCR assay, include, the detection of live cells only, a 100-1000 fold increase in sensitivity, and elimination of PCR inhibitors associated with plant samples thereby eliminating false negatives. Methods for conducting BIO-PCR are described in U.S. Pat. No. 6,410,223.

In another embodiment, the present invention relates to a method of detecting *Acidovorax avenae* subsp. *citrulli* in a test sample. This method uses the amplification methods previously described herein. Generally, DNA amplification involves the following steps: (a) providing a test sample comprising bacterial cells or microorganisms or extracted DNA for standard PCR or bacterial cells or microorganisms amplified by growing on an agar medium for BIO-PCR that is suspected of containing DNA from *Acidovorax avenae* subsp. *citrulli*; (b) amplifying a target sequence of the DNA with the primers of the present invention under amplification conditions to provide DNA amplification products carrying the selected target DNA sequence; and (c) detecting the presence of the DNA amplification products as an indication of the presence of live *Acidovorax avenae* subsp. *citrulli* in the test sample.

As discussed briefly above, the test sample can be bacterial cells or microorganisms or extracted DNA. The extracted DNA can be from any biological sample, such as from a plant, bacterial cells, microorganism, etc. Extraction of DNA from a biological sample can be conducted using routine techniques known in the art.

If PCR is to be used to detect *Acidovorax avenae* subsp. *citrulli* in a test sample, the test sample can be provided in an aqueous buffer formulated with an effective amount of $Mg_2$ co factor. Additionally, the reaction is conducted with an effective amount of a DNA polymerase (such as Taq DNA polymerase, which can be in the form of native purified enzyme or a synthesized form such as AMPLITAQ (which is available from Applied Biosystems, Foster City, Calif.)), an effective amount of deoxynucleotide triphosphates (i.e., dATP, dCTP, dGTP, and dTTP) or nucleotide analogs (dNTPs) as a nucleotide source in a saturating concentration and an effective amount of one or the pair of primers described herein. Alternatively, PCR premixes, which contain buffer, dNTPs and Taq polymerase as a premixed reagent can be used. If such a premix were used, an effective amount of one or the pair of primers described herein would need to be added.

Methods for setting up a PCR reaction are well known to those skilled in the art. Specifically, a buffered reaction mixture is prepared that contains the DNA substrate to be amplified, the primer or primers, Me cofactor, dNPTs and Taq polymerase. Prior to the PCR cycling, a single step is usually performed to denature the DNA substrate. This step usually is performed between about 92° C. to about 95° C. for about 2 to about 10 minutes. Following this initial denaturation step, a cycling process occurs to amplify the target sequence. The number of cycles typically varies between about 25 to about 40, and there normally are 2 or 3 steps in each cycle. During each cycle, three things happen. The first step denatures both the original DNA substrate, and any nascently formed products. This step requires between 10 seconds and several minutes at about 92° C. to about 95° C. Following the denaturation step, the primers have to anneal to their complementary regions of the target sequence, and then the DNA polymerase needs to extend the primers to synthesize the desired product. Depending on the melting temperature of the primers, this can be accomplished in one, or two steps. After the primer(s) are annealed to the target, the optimum temperature to extend these primers using Taq polymerase is about 72° C. If the $T_m$ of the primers is close to this temperature, both the annealing and synthesis steps can be performed at the same time, resulting is a two-step cycle (denaturation followed by annealing/synthesis). If the $T_m$ of the primers is much lower than about 72° C., it is common to have a three step cycle. In a three step cycle, there is a denaturation step, a primer annealing step, and a extension step. Each of these steps can be between 10 seconds and 2 minutes. An example of a 3 step reaction would be 30 seconds at about 95° C., 30 seconds at about 55° C., and 60 seconds at about 72° C.

If *Acidovorax avenae* subsp. *citrulli* is present in the test sample, a single amplification product results. This amplification product is about 200-300 base pairs in length, preferably about 232 base pairs in the length, whose termini are defined by the oligonucleotide primer(s) of the present invention and whose length is defined by the distance between the two primers or the length of time of the amplification reaction. This polynucleotide sequence (i.e., the amplification product) then serves as a template for the next reaction.

The amplification product can be separated from the reaction mixture and analyzed. The amplified polynucleotide sequence can be analyzed using techniques known in the art, such as gel electrophoresis or other techniques known in the art. Additionally, the amplified polynucleotide sequence can be directly or indirectly labeled using techniques known in the art. A far more stringent way to verify the amplification product is to sequence the product.

To verify the identity of the amplification product, a Southern blot assay can be conducted. In a Southern blot assay, the amplification products are separated by electrophoresis, transferred to a membrane (i.e. nitrocellulose, nylon, etc.), reacted with an oligonucleotide probe or any portion of the DNA sequence of interest. The probe is then modified to enable detection. The modification methods can be the incorporation of a radiolabeled nucleotide or any number of non-radioactive labels (such as biotin).

The oligonucleotide probe used in the Southern blot assay is derived from the genomic DNA sequence of *Acidovorax avenae* subsp. *citrulli* and hence is specific for DNA from *Acidovorax avenae* subsp. *citrulli*. The probe used in the Southern blot assay can be prepared using routine, standard methods. For example, the probe can be isolated, cloned and restricted using routine techniques known in the art or can be made using the chemical synthesis methods described previously herein.

Alternatively, the amplification products can be detected using dot blot analysis. Dot blot analysis involves adhering an oligonucleotide probe (such as the one described previously) to a nitrocellulose or solid support such as, but not limited to, a bead (such as, but not limited to, polystyrene beads, magnetic beads or non-magnetic beads, etc), walls of a reaction tray, strips (such as, but not limited to nitrocellulose strips), test tube. The sample containing the labeled amplification product is added, reacted, washed to removed unbound sample, and a labeled, amplified product attached to the probe is visualized using routine techniques known in the art.

The detection of the amplification product in the sample provides evidence of the presence of *Acidovorax avenae* subsp. *citrulli* in the test sample. If BIO-PCR is used, the method described herein can be used to identify the presence of viable cells of *Acidovorax avenae* subsp. *citrulli*. As described in U.S. Pat. No. 6,146,834, detection utilizing BIO-PCR can be enhanced further when combined with the "Taq-Man" detection system which is described in Holland et al., *Proc. Natl. Acad. Sci. USA,* 88:7276-7280 (1991). TaqMan is a PCR based assay that is modified to contain a "fluorescent reporter" and a "fluorescent quencher" pair at the 5' and 3' termini. Typically, this probe about is 8 to about 25 nucleotides in length, which positions the quencher close enough to the reporter to quench the reporter signal. If this probe anneals to the target sequence during PCR, the 5' to 3' exonuclease activity of the DNA polymerase causes the reporter and quencher to be untethered, resulting in a recordable fluorescent signal that is proportional to the amount of target signal being amplified.

In yet another embodiment, the present invention relates to a method of evaluating or monitoring the efficacy of treatments being utilized to eliminate *Acidovorax avenae* subsp. *citrulli* from a seed lot. The method involves obtaining a first test sample from a seed lot suspected of containing *Acidovorax avenae* subsp. *citrulli*. Once this first test sample is obtained, DNA is extracted from the test sample using routine techniques known in the art or bacterial cells or microorganisms from the test sample suspected of containing DNA of *Acidovorax avenae* subsp. *citrulli* are supplied for use in an amplification method (i.e., PCR or BIO-PCR). The extracted DNA or bacterial cells or microorganisms suspected of containing DNA of *Acidovorax avenae* subsp. *citrulli* are then amplified (i.e. using PCR or BIO-PCR) using primers having the sequence of 5'-CGCGCCGACCGAGACCTG-3' (SEQ. ID NO:1) and 5'-GGGGCACGCCAACATCCT-3' (SEQ. ID NO:2). Then, the presence of the amplification product(s) of the target DNA is then detected using the techniques described herein. The presence of the amplification product(s) of the target DNA is confirmation of the presence of *Acidovorax avenae* subsp. *citrulli.*

If the presence of *Acidovorax avenae* subsp. *citrulli* in the first sample is confirmed, then the seed lot from which the first sample was obtained or a portion of that seed lot can be treated with a composition to reduce or eradicate *Acidovorax avenae* subsp. *citrulli*. Such compositions are well known in the art and include, but are not limited to, peroxyacetic acid. After a sufficient period of time has elapsed to allow such treatment to take effect, a second test sample is taken from the treated seed lot or treated portion thereof. As with the first test sample, DNA is extracted from the second test sample using routine techniques known in the art or bacterial cells or microorganisms from the second test sample are supplied for use in an amplification method. The extracted DNA or cells or microorganisms are then amplified (i.e. using PCR or BIO-PCR) for target DNA *Acidovorax avenae* subsp. *citrulli* of using primers having the polynucleotide sequence of 5'-CGCGCCGACCGAGACCTG-3' (SEQ. ID NO:1) and 5'-GGGGCACGCCAACATCCT-3' (SEQ. ID NO:2) under amplification conditions. Then, the presence of the amplification product(s) of the target DNA is then detected using the techniques described herein. Finally, the amount of the amplification product(s) or absence of amplification product(s) in the second test sample is compared to the amount of amplification product(s) in the first test sample. If the amount of amplification product(s) is less than the amount of amplification product(s) in the first test sample or if there is no amplification product(s) in the second test sample, this provides evidence that the treatment protocol being utilized to eliminate *Acidovorax avenae* subsp. *citrulli* seed lot is efficacious. If the amount of amplification product(s) is more than the amount of amplification product(s) in the first test sample, this provides evidence that the treatment protocol being utilized to eliminate *Acidovorax avenae* subsp. *citrulli* seed lot is not efficacious.

In yet another embodiment, the present invention relates to a test kit for identifying *Acidovorax avenae* subsp. *citrulli.* More specifically, the oligonucleotide primers and primer sets of the present invention can be packaged into kits for use in amplification methods for identifying *Acidovorax avenae* subsp. *citrulli* in a test sample. The kits will contain the primers in a premeasured or predetermined amount, as well as other suitably packaged reagents and materials, in separate suitable containers, need for the particular amplification method. For example, the kit may contain standard buffers, solid supports, enzymes, substrates, instructions, etc., for identifying *Acidovorax avenae* subsp. *citrulli* in a test sample.

By way of example, and not of limitation, examples of the present invention shall now be given.

Example 1

Development of the Primers of the Present Invention

Primers (identified as RST 90 and RST 91) supplied by R. Stall (University of Florida) were used in an amplification reaction to amplify *Acidovorax avenae* subsp. *citrulli.* A 380 base pair PCR product was obtained, cloned and sequenced, and the sequence of the product was used to develop the primers of the present invention using routine techniques known in the art such as those described in *Current Protocols in Molecular Biology*, Ausubel, Brent, Kingston, Moore, Seidman, Smith and Struhl, editors, John Wiley & Sons (1994).

More specifically, the PCR product was resolved on an agarose gel, and excised using a razor blade. Comparison of the product with molecular mass markers provided an estimate of the size of the product around 400 base pairs. Excised DNA was purified from the agarose by crushing the agarose into small pieces and centrifuging the slurry through a small column packed with glass wool.

Purified DNA was ligated into the plasmid vector pT7 Blue using the Perfectly Blunt PCR Cloning Kit, according to the Manufacturer's instructions (Novagen Inc., Milwaukee, Wis. 53288), and transformed into *Escherichia coli* (Novagen Blue). After transformation, aliquots were spread onto media plates according to the Novagen kit instructions and colonies were allowed to grow by incubating the plates overnight at 37° C.

*E. coli* clones harboring the pT7 Blue plasmid with the insert DNA were selected by color selection, and then by size selection by running digested DNAs on an agarose gel. One of these clones was selected, and renamed pSVS1224. DNA was prepared from pSVS1224 using standard methods, and the inserted DNA was sequenced using chemistry from Applied Biosystems, and resolved on an ABI377 automated sequencer (Applied Biosystems, Foster City, Calif.).

The resulting sequence, shown below, was imported into the LASERGENE molecular biology software package (LASERGENE, Madison, Wis.). The primer select module of LASERGENE was used to design new PCR primers, referred to as WFB1 (SEQ ID NO:1) and WFB2 (SEQ ID NO:2).

```
                                        (SEQ ID NO: 3)
ACATGGCCAC GGCGATGAGG ATGCCCGGCG CGAAGCCGGC

GATGAAGAGC GCGCCGACCG AGACCTGCTC GTCCTGCAGC

GCGTAGATGA TCATGATGAT CGAGGGCGGG ATGATGGGCC

CCACGATGGC CGTGCTGGCG GTGAGCGCGG CGGCGTATGC

GCGCGAGTAG CCCGCCTTGT CCATCATCTT GACCATCATC

GAGCCGGGCC CCGCCGCGTC GGCCAGGGCC GAGCCCGAGA

TGCCCGAGAA CAGCGTGAGC GACAGGATGT TGGCGTGCCC

CAGGCCCCCG CGCAGGTGGC CCACGAACTG CGCGGCGAAG

CGCAGCAGCA CCACGGTGAG CGCGCCGCCG GACATGATCT

CGGCCGCGAG GATGAAGAAG GCACGGCCAT CG
```

Example 2a

Protocol for Preparing Seed Samples Prior to PCR

A culture of *Xanthomonas campestris* pv. *vesicatoria* (Xcv) is initiated on YDC agar (hereinafter referred to as "YDC") and incubated at 28° C. If timing is such that a culture cannot be started two days ahead of the test (assay) date, then one can be initiated one day ahead with heavy streaking on YDC. The Xcv is included in the test as an added control to insure that the test is performing correctly. The test can be conducted without the inclusion of the Xcv. Initiate 3-4 tubes of Nutrient Broth with a viable culture of *Acidovorax avenae* subsp. *citrulli* (Aac) the day before the test is to be run. Place the tubes on a shaker at 37° C. at 200 rpm. Count out two (2) samples of 5,000 seeds of the seeds to been used as the negative and positive control and place in Ziplock bags. Label the bags with the appropriate sample numbers and record.

Count out the appropriate number of samples (of seed) to be tested. The number to be tested by PCR can range from about 10,000 to about 30,000 seeds with the balance being done by growout. The inspection lot and batch number are recorded on a record sheet. A separate disposable container is used to weigh each lot. Any positives obtained in the PCR test are retested at 1× in a greenhouse grow-out test.

Each subsample of 5,000 seeds is placed in a 1.0 gallon freezer Ziplock bag. Once sealed, this bag is placed inside another Ziplock bag. Both bags are labeled with the sample (batch) number.

Prepare the amount of PABST buffer needed for the number of samples to be tested. PABST is Phos-Tween (See the enclosed protocol for making Phos-Tween in Example 2d) ascorbic acid and potassium metabisulfate. PABST buffer is made fresh immediately before use (See enclosed protocol for making PABST buffer in Example 2d).

The PABST buffer is prepared by adding the ascorbic acid and potassium metabisulfite to two liters of Phos-Tween. After the chemicals are dissolved, the remaining volume of Phos-Tween is added. The pH is adjusted to about 6.5 using concentrated NaOH (approximately about 5 mls/liter of PABST).

A suspension of *Xanthomonas campestris* pv. *vesicatoria* is prepared in a 50 ml disposable sterile centrifuge tube in Phos-Tween. Enough material is used from the single colonies on a YDC culture to prepare a faintly turbid suspension. The suspension is vortexed to ensure that all the culture material is in solution. The optical density ($OD_{620}$) of the suspension is measured and adjusted to about 0.045 to about 0.055.

Vortex the nutrient broth suspension of Aac prepared previously, and add up to about 9 mls of Phos-Tween. The concentration is adjusted so that the $OD_{620}$ is between about 0.095 and about 0.105. The PhosTween is used as a reference for the spectrophotomer. A 1:10 serial dilution of the OD adjusted Aac suspension to $10^{-7}$ in 9 ml tubes of Phos-Tween.

The required amount of PABST is added to the seed samples in Ziplock bags. The bags are sealed and placed upright in plastic tubs. After the PABST is added to all bags, one ml of the previously made Xcv suspension is added to each of the bags in the assay with the exception of the positive control. The bags are closed tightly.

About 2.3 ml of the $10^{-3}$ Aac dilution tube made previously is added to the positive control. This is now the Aac positive control. The bag is sealed and all bags in the tubs are placed into the shaker. The bags are shaken for about one hour at 150 rpm at room temperature.

About 0.2 mls of the $10^{-6}$ and $10^{-7}$ dilutions of Aac are spread-plated onto 8 Nutrient Agar for each dilution. About 0.2 mls of the $10^{-6}$ dilution are spread onto 4 Tween plates. The spread-plates are incubated for 24-48 hours at about 28° C. After incubation, the colony numbers are counted for calculation of the actual number of cells added to the control seed.

The inner bag of seed from the Ziplock bags is removed and placed into funnels. Two or three small vertical slits are cut into one of the bottom corners and the liquid rinsate is collected by allowing it to drain into a centrifuge bottle (such as a 250 ml centrifuge bottle). The seed is discarded. The centrifuge bottles are balanced for centrifuging. If necessary, a small amount of PABST can be added. Centrifuge the rinsate, such as in a GSA rotor in a Sorvall RC-5B centrifuge, for about 5 minutes at 2500 rpm to pellet the soil and debris. Transfer the supernatant into a clean centrifuge bottle, such as a 250 ml centrifuge bottle. Decant slowly so that if the pellet is soft pieces of the pellet will not accompany the supernatant. If necessary, leave a few milliliters of solution in the bottle to avoid particulates. Centrifuge the filtrate, such as in a GSA rotor in a Sorval RC-5B centrifuge), for about 15 minutes at 5,600 rpm to pellet the bacteria. Discard the supernatant carefully and preserve the pellet. If necessary, leave a few milliliters of solution in a bottle to avoid discarding the soft pellet pieces. About 0.5 grams of polyvinylpyrolidone (PVPP; see protocol in Example 2d) is added to each centrifuge bottle. Add the contents of a 5 ml tube of Phos-Tween into the centrifuge bottle and resuspend the pellet. This suspension is incubated at room temperature for about 30 minutes. After about 30 minutes, the suspension is poured through a Miracloth (Calbiochem, San Diego, Calif.) and collected in a centrifuge tube. The resulting liquid fraction is then centrifuged for about 15 minutes at 7,000 rpm using a SA600 rotor to pellet the bacterial cells. Discard the supernatant. Resuspend the pellet in about 1.3 mls of Phos-Tween, although less can be used if liquid is retained in the tube. This final suspension is now ready for DNA extraction.

Example 2b

DNA Extraction

The final suspension from Example 2a is centrifuged using an Eppendorf 5415C centrifuge and rotor at about 16,000 g for about 2 minutes. The supernatant is discarded and the pellet resuspended in about 582 μl of TE buffer (See Example 1d for protocol for TE buffer). Add about 15 μl of 20% sodium dodecyl sulfate (SDS) and about 3 μl of Proteinase K (See Example 2d) and the suspension is incubated at 37° C. for about 1 to about 1.5 hours. Add about 100 μl of 5M NaCl and 80 μl of hexadecyltrimethylammonium bromide (CTAB) (See Example 2d). The suspension is incubated in a water bath at 65° C. for about 15 minutes. Add about 770 μl of chloroform-isoamyl alcohol (24:1) (See Example 2d). The suspension is mixed for about 15 minutes then centrifuged for about 5 minutes at about 16,000 g using an Eppendorf 5417C centrifuge and rotor. The aqueous supernatant is discarded and placed into a 2 ml tube. About 500 μl of phenol/chloroform/isoamyl alcohol (25:24:1) is added. The suspension is mixed for about 15 minutes and then centrifuged for about 15 minutes at about 16,000 g using a an Eppendorf 5417C centrifuge and rotor. About 550 μl of supernatant is transferred to a 1.5 ml tube. About 550 μl of cold isopropyl alcohol is added. The suspension is mixed and stored for at least about four (4) hours at about −80° C.

The samples are removed from storage, thawed and centrifuged for about 30 minutes at about 16,000 g using a an Eppendorf 5417C centrifuge and rotor. Discard the supernatant and wash the pellet with about 500 μl of 70% ethanol. Centrifuge the sample for about 10 minutes at about 16,000 g using an Eppendorf 5417C centrifuge and rotor. Remove the supernatant and dry the pellet in a vacuum dessicator for about 10 minutes. Redissolve the pellet in about 100 μl of TE buffer and incubate the samples in a 65° C. water bath. Vortex and mix the samples well. Make a 1:50 dilution of the resuspended DNA in water and run about 50 μl through a BioRad Microspin column.

Example 2c

PCR

Load 5 μl of the DNA suspension from Example 2b into each of the two tubes of PCR reaction mixture. Each reaction well contains: 5 μl of 10×PCR buffer (Perkin Elmer), 8 μl of 1.25 mM dNTPs, 3.3 μl of $MgCl_2$, 1 μl at 5 pmol/μl of each of SEQ ID NO:1 and SEQ ID NO:2, 0.25 of Taq polymerase, and 26.45 μl of water. Each sample tube is run in a PCR thermocycler (Perkin Elmer GeneAmp PCR System 9600 or an Applied Biosystems GeneAmp PCR System). The amplifications were conducted under the following conditions: initial DNA denaturation for 10 minutes at about 93° C., followed by a cycling step of about 95° C. for 1 minute, 62.1° C. for 30 seconds, 72° C. for about 30 seconds. The PCR cycle is repeated for about 35 cycles. After cycling, there is a final extension step of about 5 minutes at 72° C. followed by storage of the products at 4° C. until they are removed from the PCR machine. To detect a product, 10 μl of loading dye (defined below) is added to each reaction well. About 16 μl of PCR reaction is added to an electrophoresis gel containing 2% Seakem LE (defined below) agarose in 0.5×TBE buffer (see Example 2d) and electrophoresed. as described in Maniatis et al., *Molecular Cloning, a Laboratory Manual*, Cold Spring Harbor Laboratory, Cold Spring Harbor, N.Y. (1989). The gel consists of 2% Seakem LE in TBE buffer (See Example 2d). The gel is run at 80 or 120 volts depending on the size of the gel.

Example 2d

Buffers and Reagents

| Protocol for making Phos-Tween and 1L of PABST | |
|---|---|
| In 200.0 ml MM $H_20$ dissolve: | |
| Potassium Phosphate ($K_2HPO_4$•$3H_20$) | 1.96 g |
| Potassium Phosphate ($KH_2PO_4$) | 0.994 g |
| Tween 20 | 0.20 ml |
| Bring volume up to 1.0 L | |
| Adjust pH = 6.5 | |
| (using 5M HcL.) | |
| At this point this mixture is known as 'Phos-Tween' | |
| Sterilize | |
| Before using add: | |
| L-Ascorbic Acid ($C_6H_8O_6$) | 17.6 g |
| Potassium Metabisulfite ($K_2O_5S_2$) | 2.2 g |
| Adjust pH = 6.5 | |
| (using NaOH) | |

This formula is now referred to as PABST.

5×TBE Stock: Tris-Borate-EDTA Buffer (pH=8.35)

Dissolve the following reagents in 800 mls MQ-water in a 2-liter flask on a stir plate;

54.0 g Trizma Base (Sigma Aldrich ("Sigma"), St. Louis, Mo., Cat. #T8524)

27.5 g Boric Acid (Sigma Cat. # B-6768)

20 mls 0.5M (Ethylenedinitrilo) tetraacetic acid disodium salt (EDTA) stock pH=8.0

Adjust the total volume to 1.0 liter

| Handling | Autoclaved | U.V. light | filter sterilized | aliquot volume |
|---|---|---|---|---|
| YES | | | | |
| NO | XX | XX | XX | XX |

10× Tris-Acetate-EDTA buffer stock

Dissolve the following in 800 mls MQ-water in a 2 liter flask on a stir plate;

48.4 g Trizma Base (Sigma cat. # T-8524)

11.42 mls glacial acetic acid (Sigma cat. # A6283)

20 mls 0.5M EDTA

Adjust the volume to 1.0 liter

Because this stock is highly concentrated it may need extra time on the stir plate to completely come to solution.

| Handling | Autoclaved | U.V. light | filter sterilized | aliquot volume |
|---|---|---|---|---|
| YES | | | | |
| NO | XX | XX | XX | XX |

1× Tris-Acetate-EDTA (TAE) Buffer

Mix 100 mls of 10×TAE and 900 mls of MQ-water.

| Handling | Autoclaved | U.V. light | filter sterilized | aliquot volume |
|---|---|---|---|---|
| YES | | | XX | |
| NO | XX | XX | | XX |

PABST buffer: BFB-PCR seed wash buffer

Dissolve 17.6 g Ascorbic Acid (Sigma cat. # A-7506) and 2.2 g

Potassium Metabisulfite (Sigma cat. # P-2522) in 1.0 liter of Phos

Tween buffer. Adjust the pH to 6.50 with Saturated NaOH.

| Handling | Autoclaved | U.V. light | filter sterilized | aliquot volume |
|---|---|---|---|---|
| YES | XX | | | 5, 9 & 15 mls/tube |
| NO | | XX | XX | Also 2 liter bottler |

5.0M NaCl: Sodium Chloride

Dissolve 29.22 g of NaCl (available from VWR International, West Chester, Pa., cat. # VW 6430-7) in 80 mls of MQ water. Adjust the volume to a total of 100 mls.

| Handling | Autoclaved | U.V. light | filter sterilized | aliquot volume |
|---|---|---|---|---|
| YES | XX | XX | | 1.5 mls/tube |
| NO | | | XX | |

CTAB/NaCl: Hexadecyltrimethylammonium Bromide/Sodium Chloride solution.

Dissolve 4.1 g NaCl (available from VWR International cat. # VW 6430-7) and 10 g CTAB (Sigma cat. # H-6269) in 100 mls of MQ water. Mix the reagent by spinning on a stir plate with mild heat until the crystals are completely dissolved.

| Handling | Autoclaved | U.V. light | filter sterilized | aliquot volume |
|---|---|---|---|---|
| YES | | XX | | 1.2 mls/tube |
| NO | XX | | XX | |

TE buffer: Tris-EDTA

Dissolve 0.394 g Trizma Hydrochloride (Sigma cat. # T-7419) and 1.0 mls of 0.25M EDTA stock in 250 mls MQ water. Adjust the pH to 8.0 using 1.0 M NaOH.

| Handling | Autoclaved | U.V. light | filter sterilized | aliquot volume |
|---|---|---|---|---|
| YES | XX | XX | | 1.5 mls/tube and 16 mls/vial |
| NO | | | XX | |

70% Ethanol

Add 70.0 mls of 100% ethanol to 30.0 mls of MQ water in the hood and invert to mix.

| Handling | Autoclaved | U.V. light | filter sterilized | aliquot volume |
|---|---|---|---|---|
| YES | | | | 12.0 mls/vial |
| NO | XX | XX | XX | |

20% SDS: Sodium Dodecyl Sulfate (This reagent is found as Lauryl Sulfate disodium salt (Sigma cat. # L-4390). Dissolve 5.0 g SDS in 25.0 mls of MQ water. In order to mix this reagent properly add a stir bar to the bottle and stir on a hot plate over medium-low heat.

| Handling | Autoclaved | U.V. light | filter sterilized | aliquot volume |
|---|---|---|---|---|
| YES | | XX | | 320 mls/tube |
| NO | XX | | XX | |

1.0M $MgCl_2$: Magnesium Chloride

Dissolve 20.33 g $MgCl_2.6H_2O$ (Sigma cat #M-2670) in 80.0 mls of MQ water. Adjust the volume to 100.0 mls total with MQ water.

| Handling | Autoclaved | U.V. light | filter sterilized | aliquot volume |
|---|---|---|---|---|
| YES | | | XX | |
| NO | XX | XX | | XX |

PVPP: Polyvinylpolypyrrolidone (Sigma cat. # P-6755) for BFB-PCR test. This protocol is taken from Holben et al (Appl. Environ. Microbiol. 54:703-711 (1988)).

1—Mix 300.0 gms of PVPP in 4 liters of 3.0 M Hydrochloric acid. The HCl. is prepared by diluting concentrated Hcl (12.1N)

2—Mix and let sit at room temperature in a fume hood for 12-16 hrs with occasional gentle stirring.

3—Filter sterilized the suspension through Miracloth (Calbiochem, San Diego, Calif., Calbiochem cat. #475855). Gentle squeezing of the Miracloth can be done to remove most of the liquid. Eventually the Miracloth will tear, be careful not to lose any PVPP.

4—Resuspend the PVPP in 4.0 liters of 20 mM Potassium Phosphate buffer, pH=7.4. Prepare the buffer by adding 10.89 gms of $KH_2PO_4$ to a total of 4.0 liters of MQ water. Adjust the pH to 7.4 using 8.0 M KOH (~10 mls).

5—Soak at room temperature for 1-2 hrs, gently stirring occasionally.

6—Filter sterilized the suspension through Miracloth as in step 3.

7—Repeat steps 4 through 6 until the pH of the suspension reaches 7.0 (4 to 5 times).

8—Filter sterilized through Miracloth as in step 3.

9—Spread the PVPP out into a thin layer on aluminum foil and dry in a flow hood overnight. Material can be stored in a capped jar and is useful for extended periods of time, >1 year.

Starting with 300 grams, yield should be ~280 gms after the procedure is completed.

| Handling | Autoclaved | U.V. light | filter sterilized | aliquot volume |
|---|---|---|---|---|
| YES | | | | 0.5 grams/bag |
| NO | XX | XX | XX | |

Chloroform-Isoamyl Alcohol: BFB-PCR DNA extraction.

This reagent comes prepared from Sigma (Sigma cat. # C-0549).

| Handling | Autoclaved | U.V. light | filter sterilized | aliquot volume |
|---|---|---|---|---|
| YES | | | | 16.0 mls/vial |
| NO | XX | XX | XX | |

Phenol-Chloroform-Isoamyl Alcohol: BFB-PCR DNA extraction. This reagent comes from Sigma (Sigma cat.# P-2069) with its own equilibration buffer. Add the equilibration buffer to the bottle of Phenol-Chloroform-Isoamyl Alcohol, invert several times to mix, and let the bottle equilibrate in the negative pressure hood for about 2 hours.

| Handling | Autoclaved | U.V. light | filter sterilized | aliquot volume |
|---|---|---|---|---|
| YES | | | | 12.0 mls/vial |
| NO | XX | XX | XX | |

6× Gel loading dye: To run DNA samples on agarose gels.

This reagent comes prepared from Sigma (Sigma cat. # G-7654).

| Handling | Autoclaved | U.V. light | filter sterilized | aliquot volume |
|---|---|---|---|---|
| YES | | | | 2.0 mls/tube |
| NO | XX | XX | XX | |

Proteinase K: BFB-PCR and PFGE DNA extraction.

This reagent comes prepared from Sigma (Sigma cat. # P-2308). The reagent comes as a lyophilized powder in 100 mg quantity. Add 5.0 mls of sterile MQ water to the vial, cap tightly, and invert several times to bring the powder to solution. This is a 20 mg/ml stock ready for aliquotting or direct use.

| Handling | Autoclaved | U.V. light | filter sterilized | aliquot volume |
|---|---|---|---|---|
| YES | | | | 63.0 mls/tube |
| NO | XX | XX | XX | |

Isopropanol: For precipitation of DNA during extraction.

This reagent comes prepared from Sigma (Sigma cat. # 1-9516).

| Handling | Autoclaved | U.V. light | filter sterilized | aliquot volume |
| --- | --- | --- | --- | --- |
| YES | | | | 12.0 mls/vial |
| NO | XX | XX | XX | |

Nusieve 3:1 Agarose: For restriction endonuclease gel analysis.

This reagent comes from FMC BioProducts, Rockland, Me. (FMC Bio Products cat.# 50090).

| Handling | Micro-waved | U.V. light | filter sterilized | aliquot volume |
| --- | --- | --- | --- | --- |
| YES | XX | | | |
| NO | | XX | XX | XX |

Seakem LE: Agarose for analyzing PCR samples.

This reagent comes from FMC BioProducts (FMC Bio-Products cat.# 50004).

| Handling | Micro-waved | U.V. light | filter sterilized | aliquot volume |
| --- | --- | --- | --- | --- |
| YES | XX | | | |
| NO | | XX | XX | XX |

+PCR 100 bp low Ladder: A size standard for running agarose gels. This reagent comes prepared from Sigma (Sigma cat. # P-1473). In order to dilute the ladder for use locate the concentration of the ladder on the label, for example 102 μg/ml or 102 ng/mμl. The ladder should be run at 50 ng/μl. There is 40 μg of total DNA in the tube before dilution. Therefore, 40 μg÷102 μg/ml=0.392 mls or 392 μls of ladder stock and 102 μg/m≧50 μg/ml=2.04-fold dilution of the ladder stock to reach the proper concentration for use.

2.04*392 μls=799.68 μls or 800.0 μls total volume after dilution. So, 800 μls-392 μls=408 μls this is the total volume of TE+gel loading dye that needs to be added to properly dilute the ladder. 800 μls+6=133.3 μls of gel loading dye (6× concentrate)

So, 392 μls+133 μls=525 μls and 800 μls-525 μls=275 μls of TE.

Thus, the final composition of the diluted ladder is 392 μls of ladder stock (i.e. the entire vial) plus 133 μls of 6× gel loading dye plus 275 μls of TE buffer. Aliquot the ladder into 250 μl tubes, approximately 200 μls per tube. Store three tubes at −20° C. for long term storage and leave a single tube at 4° C. for general use. Use 5 μls per lane on a 2% agarose gel.

| Handling | Autoclaved | U.V. light | filter sterilized | aliquot volume |
| --- | --- | --- | --- | --- |
| YES | | | | 250 mls/tube |
| NO | XX | XX | XX | |

Example 3

Testing of Commercial Seed Lots for the Presence of the Bacterium Aac

Figure 3C:
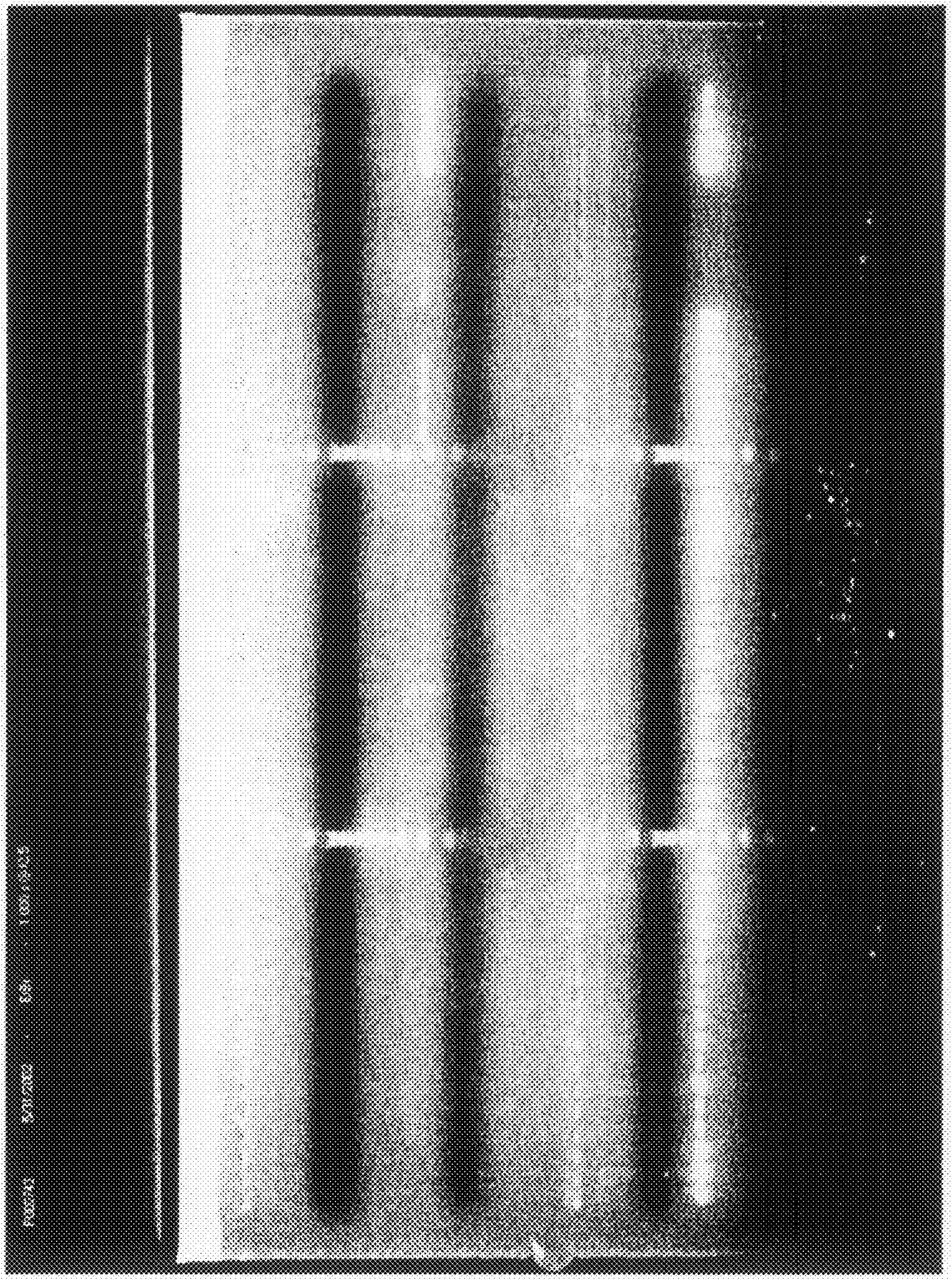

The seed in the bags listed below were each subjected to the seed wash protocol described in Example 2a, subjected to DNA extraction as described in Example 2b. PCR was conducted as described in Example 2c. The results are provided below. The results of the PCR and gel electrophoresis are provided in FIGS. 3*a*-3*c*.

Type of Seed: Watermelon. Number of seed per bag: 5,000.

| Batch# | Bag/Sample #s | Vol. PABST/Bag | Final Result |
| --- | --- | --- | --- |
| 628626 | 1 & 2 | 600 | Both Bags NEG |
| 628626 | 3 & 4 | 600 | Both Bags NEG |
| 628640 | 5 & 6 | 600 | Both Bags NEG |
| 540141 | 7 & 8 | 600 | Both Bags NEG |
| 628625 | 9 & 10 | 600 | Both Bags NEG |
| 628625 | 11 & 12 | 600 | Both Bags NEG |
| 619603 | 13 & 14-17 | 600 | Both Bags NEG |
| 619584 | 15 & 16-18 | 600 | Both Bags NEG |
| Additional Aac Bags #17 & 18 | 17 & 18 | | Both Bags POS Check |
| Sugar Baby[1] | 19 & 20 | 600 | NEG (Bag 19) POS (Bag 20) |

NEG = NEGATIVE for Aac +200 mls extra
POS = POSITIVE for Aac
[1]Control (Commercially Available from Seminis Vegetable Seeds, Inc)
Total PABST 6,200 mls.

| PABST Buffer | Calls for | Amount weighed |
| --- | --- | --- |
| Ascorbic acid (17.6 g/l) | 109.12 | 109.12 |
| Potassium Metabisulfite (2.2 g/l) | 13.64 | 13.64 |
| PH | 6.50 | 6.50 |

Optical Density @ 620 nm, Stock Aac suspension = 0.107
Colony Counts (48 hours):

| Sample # | $10^{-6}$ | $10^{-7}$ |
| --- | --- | --- |
| 1 | 132 | 11 |
| 2 | 104 | 13 |
| 3 | 98 | 7 |
| 4 | 92 | 6 |
| 5 | 87 | 9 |
| 6 | 110 | 7 |
| 7 | 82 | 8 |
| 8 | 102 | 10 |
| Total | 807 | 71 |
| Average | 100.8 | 8.8 |

Stock population of Aac = (Average)(5)(*Countable dilution) = 1159200 cfu
__3864______CFU/ml Seed wash
__5654______CFU/gram seed
Spike was made with 2.3 mls of the $10^{-3}$ dilution tube.
The dilution rate which gave bacteria counts between 30 & 300.

Example 4

This Example describes the random testing of commercial seed lots for the presence of the bacterium Aac.

Type of Seed: Watermelon. Number of seed per bag: 5,000.

Figure 4C:
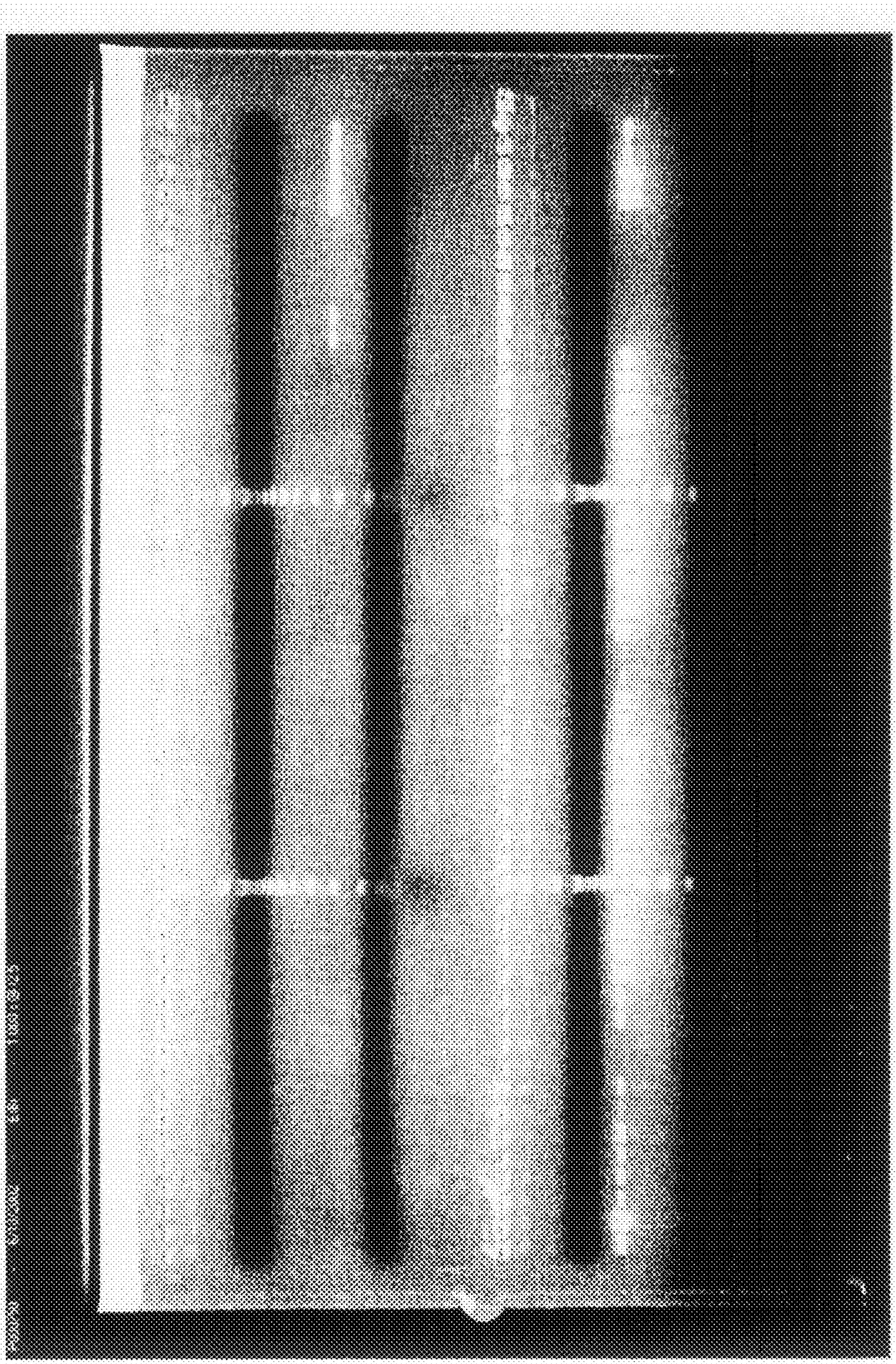

The seeds in the bags listed below were each subjected to the seed wash protocol described in Example 2a, subjected to DNA extraction as described in Example 2b. PCR was conducted as described in Example 2c. The results of such analysis is provided below. The results of the PCR and gel electrophoresis are provided in FIGS. 4*a*-4*c*.

| Batch# | Bag/Sample #s | Vol. PABST/Bag | Final Result |
|---|---|---|---|
| 583268 | 1 & 2 | 600 | Both Bags NEG |
| 583268 | 3 & 4 | 600 | Both Bags NEG |
| 634949 | 5 & 6 | 600 | Both Bags NEG |
| 634949 | 7 & 8 | 600 | Both Bags NEG |
| 628640 | 9 & 10 | 600 | Both Bags NEG |
| 628640 | 11 & 12 | 600 | Both Bags NEG |
| 540141 | 13 & 14 | 600 | Both Bags NEG |
| 540141 | 15 & 16 | 600 | Both Bags NEG |
| 583266 | 17 & 18 | 600 | Both Bags NEG |
| Sugar Baby[1] | 19 & 20 | 600 | NEG Bag (19) POS Bag (20) |

NEG = NEGATIVE for Aac +200 mls extra
POS = POSITIVE for Aac
[1]Control
Total PABST 6,200 mls

| PABST Buffer | Calls for | Amount weighed |
|---|---|---|
| Ascorbic acid (17.6 g/l) | 109.12 | 109.12 |
| Potassium Metabisulfite (2.2 g/l) | 13.64 | 13.64 |
| PH | 6.50 | 6.50 |

Optical Density @ 620 nm, Stock Aac suspension = 0.103
Colony Counts (48 hours):

| Sample # | $10^{-6}$ | $10^{-7}$ |
|---|---|---|
| 1 | 60 | 4 |
| 2 | 59 | 3 |
| 3 | 67 | 6 |
| 4 | 55 | 7 |
| 5 | 72 | 8 |
| 6 | 54 | 6 |
| 7 | 62 | 7 |
| 8 | 57 | 10 |
| Total | 486 | 51 |
| Average | 60.75 | 6.37 |

Stock population of Aac = (Average)(5)(*Countable dilution) = 699200 cfu
__2330______CFU/ml Seed wash
__3410______CFU/gram seed
Spike was made with 2.3 mls of the $10^{-3}$ dilution tube.
*The dilution rate which gave bacteria counts between 30 & 300.

Example 5

Testing of Commercial Seed Lots for the Presence of the Bacterium Aac

Figure 5C:
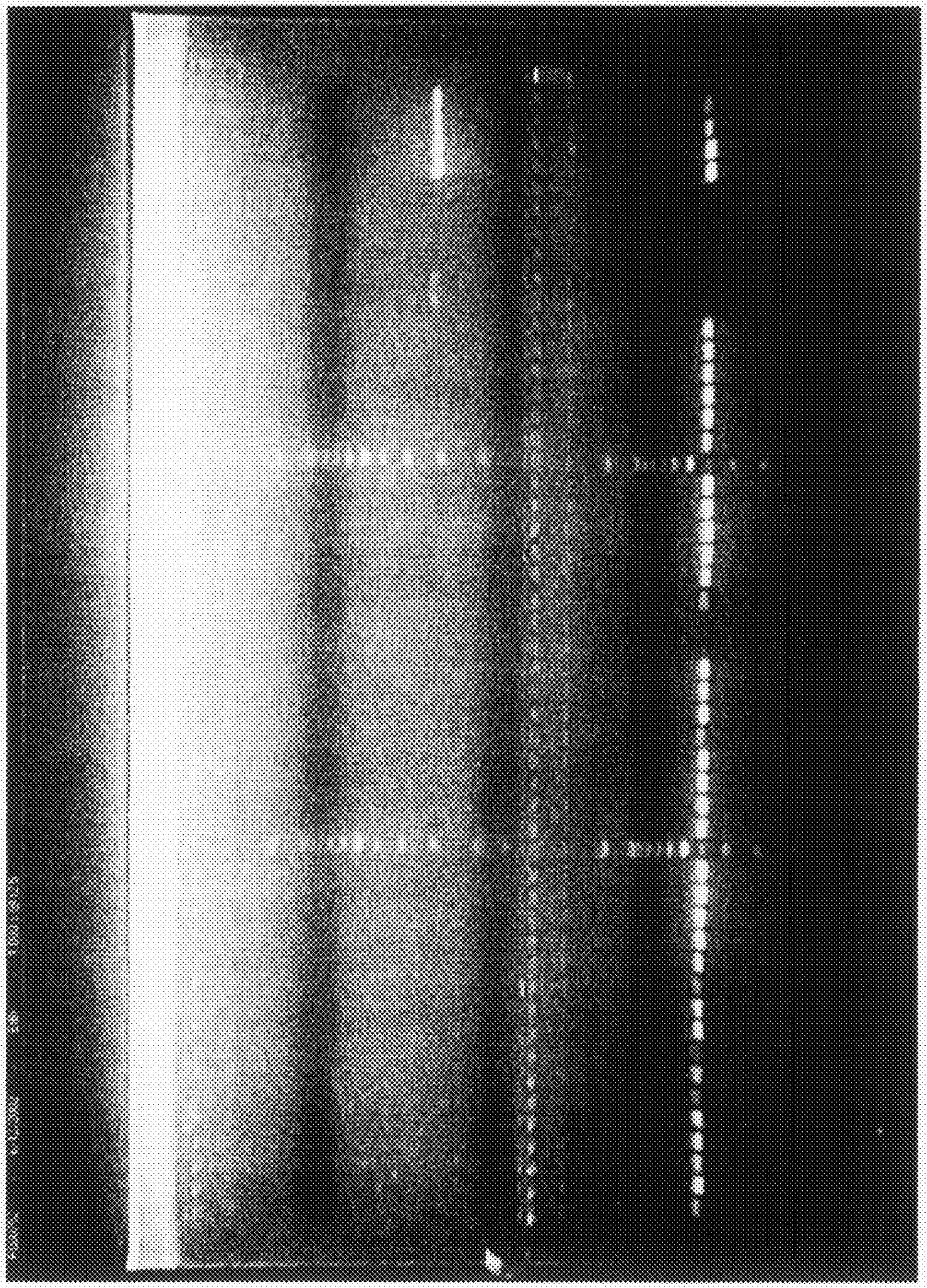

The seed in the bags listed below were each subjected to the seed wash protocol described in Example 2a, subjected to DNA extraction as described in Example 2b. PCR was conducted as described in Example 2c. The results are provided below. The results of the PCR and gel electrophoresis are provided in FIGS. 5*a*-5*c*.

Type of Seed: Watermelon. Number of seed per bag: 5,000.

| Batch # | Bag/Sample #s | Vol. PABST/Bag | Final Result |
|---|---|---|---|
| 539379 | 1 & 2 | 600 | Both Bags NEG |
| 610419 | 3 & 4 | 600 | Both Bags NEG |
| 610419 | 5 & 6 | 600 | Both Bags NEG |
| 636115 | 7 & 8 | 600 | Both Bags NEG |
| 636115 | 9 & 10 | 600 | Both Bags NEG |
| 616997 | 11 & 12 | 600 | Both Bags NEG |
| 616997 | 13 & 14 | 600 | Both Bags NEG |
| 628627 | 15 & 16 | 600 | Both Bags NEG |
| 628627 | 17 & 18 | 600 | Both Bags NEG |
| Sugar Baby[1] | 19 & 20 | 600 | NEG (Bag 19) POS (Bag 20) |

NEG = NEGATIVE for Aac +200 mls extra
POS = POSITIVE for Aac
[1]Control
Total PABST 6,200 mls

| PABST Buffer | Calls for | Amount weighed |
|---|---|---|
| Ascorbic acid (17.6 g/l) | 109.12 | |
| Potassium Metabisulfite (2.2 g/l) | 13.64 | |
| PH | 6.50 | |

Optical Density @ 620 nm, Stock Aac suspension = 0.105
Colony Counts (48 hours):

| Sample # | $10^{-6}$ | $10^{-7}$ |
|---|---|---|
| 1 | 107 | 6 |
| 2 | 82 | 9 |
| 3 | 89 | 9 |
| 4 | 73 | 11 |
| 5 | 91 | 9 |
| 6 | 97 | 10 |
| 7 | 69 | 7 |
| 8 | 84 | 7 |
| Total | 692 | 68 |
| Average | 86.5 | 8.5 |

Stock population of Aac = (Average)(5)(*Countable dilution) = 993600 cfu
__3312______CFU/ml Seed wash
__4846______CFU/gram seed
Spike was made with 2.3 mls of the $10^{-3}$ dilution tube.
*The dilution rate which gave bacteria counts between 30 & 300.

Example 6

Testing of Commercial Seed Lots for the Presence of the Bacterium Aac

Figure 6C:
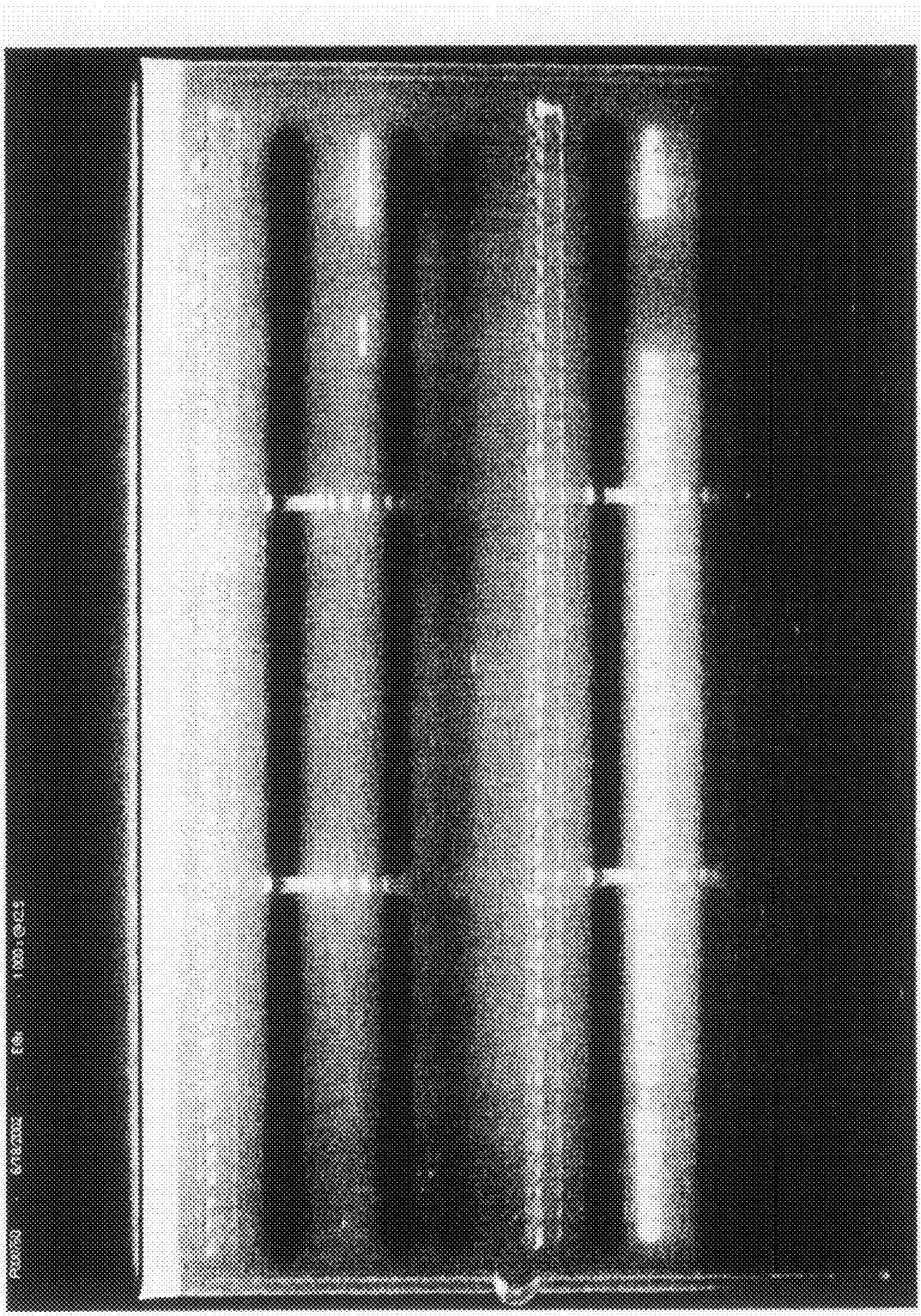

The seed in the bags listed below were each subjected to the seed wash protocol described in Example 2a, subjected to DNA extraction as described in Example 2b. PCR was conducted as described in Example 2c. The results are provided below. The results of the PCR and gel electrophoresis are provided in FIGS. 6*a*-6*c*.

Type of Seed: Watermelon. Number of seed per bag: 5,000.

| Batch# | Bag/Sample #s | Vol. PABST/Bag | Final Result |
|---|---|---|---|
| 539379 | 1 & 2 | 600 | Both Bags NEG |
| 539379 | 3 & 4 | 600 | Both Bags NEG |
| 507037 | 5 & 6 | 600 | Both Bags WEAK POS |

-continued

| | | | |
|---|---|---|---|
| 479086 | 7 & 8 | 600 | Both Bags WEAK POS |
| 641699 | 9 & 10 | 600 | Both Bags NEG |
| 641696 | 11 & 12 | 600 | Both Bags NEG |
| 574454 | 13 & 14 | 600 | Both Bags WEAK POS |
| 151342 | 15 & 16 | 600 | Both Bags WEAK POS |
| 561864 | 17 & 18 | 600 | Both Bags NEG |
| Sugar Baby[1] | 19 & 20 | 600 | NEG (Bag 19) POS (Bag 20) |

NEG = NEGATIVE for Aac +200 mls extra
POS = POSITIVE for Aac
[1]Control
Total PABST 6,200 mls

| PABST Buffer | Calls for | Amount weighed |
|---|---|---|
| Ascorbic acid (17.6 g/l) | 109.12 | 109.12 |
| Potassium Metabisulfite (2.2 g/l) | 13.64 | 13.64 |
| PH | 6.50 | 6.50 |

Optical Density @ 620 nm, Stock Aac suspension = 0.102
Colony Counts (48 hours):

| Sample # | $10^{-6}$ | $10^{-7}$ |
|---|---|---|
| 1 | 47 | 11 |
| 2 | 80 | 10 |
| 3 | 52 | 10 |
| 4 | 57 | 6 |
| 5 | 60 | 5 |
| 6 | 71 | 8 |
| 7 | 63 | 5 |
| 8 | 70 | 4 |
| Total | 500 | 59 |
| Average | 62.5 | 7.37 |

Stock population of Aac = (Average)(5)(*Countable dilution) = 717600 cfu
__2392______CFU/ml Seed wash
__3500______CFU/gram seed
Spike was made with 2.3 mls of the $10^{-3}$ dilution tube.
*The dilution rate which gave bacteria counts between 30 & 300.

Example 7

Testing of Commercial Seed Lots for the Presence of the Bacterium Aac

Figure 7C:
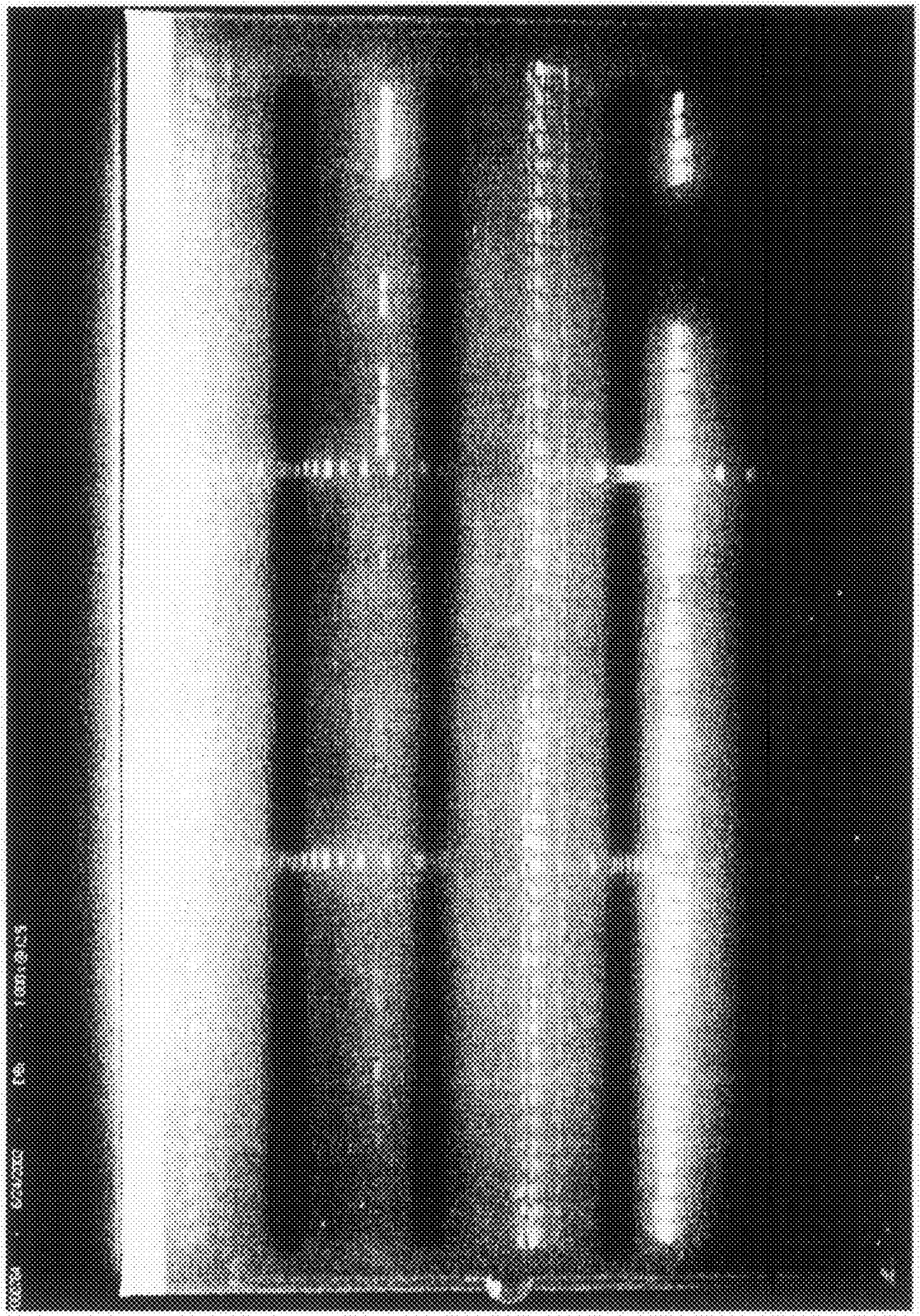

The seed in the bags listed below were each subjected to the seed wash protocol described in Example 2a, subjected to DNA extraction as described in Example 2b. PCR was conducted as described in Example 2c. The results are provided below. The results of the PCR and gel electrophoresis are provided in FIGS. 7*a*-7*c*.

Type of Seed: Watermelon. Number of seed per bag: 5,000.

| Batch# | Bag/Sample #s | Vol. PABST/Bag | Final Result |
|---|---|---|---|
| 640209[2] | 1 & 2 | 600 | Both Bags NEG |
| 520272 | 3 & 4 | 600 | Both Bags POS |
| 537894 | 5 & 6 | 600 | Both Bags POS |
| 559750 | 7 & 8 | 600 | Both Bags NEG |
| 559750 | 9 & 10 | 600 | Both Bags NEG |
| 532146 | 11 & 12 | 600 | Both Bags POS |
| 518847 | 13 & 14 | 600 | Both Bags NEG |
| 518773 | 15 & 16 | 600 | Both Bags POS |

-continued

| | | | |
|---|---|---|---|
| 506797 | 17 & 18 | 600 | Both Bags POS |
| Sugar Baby[1] | 19 & 20 | 600 | NEG (Bag 19) POS (Bag 20) |

NEG = NEGATIVE for Aac +200 mls extra
POS = POSITIVE for Aac
[1]Control
[2]Bags 1 & 2 combined contained 6,685 seeds
Total PABST 6,200 mls

| PABST Buffer | Calls for | Amount weighed |
|---|---|---|
| Ascorbic acid (17.6 g/l) | 109.12 | 109.12 |
| Potassium Metabisulfite (2.2 g/l) | 13.64 | 13.64 |
| PH | 6.50 | 6.51 |

Optical Density @ 620 nm, Stock Aac suspension = .097
Colony Counts (48 hours):

| Sample # | $10^{-6}$ | $10^{-7}$ |
|---|---|---|
| 1 | 113 | 9 |
| 2 | 97 | 13 |
| 3 | 91 | 11 |
| 4 | 120 | 13 |
| 5 | 89 | 7 |
| 6 | 106 | 9 |
| 7 | 84 | 10 |
| 8 | 94 | 12 |
| Total | 794 | 84 |
| Average | 99.2 | 10.5 |

Stock population of Aac = (Average)(5)(*Countable dilution) = 1140800 cfu
__3802______CFU/ml Seed wash
__5564______CFU/gram seed
Spike was made with 2.3 mls of the $10^{-3}$ dilution tube.
*The dilution rate which gave bacteria counts between 30 & 300.

Example 8

Testing of Commercial Seed Lots for the Presence of the Bacterium Aac

Figure 8C:
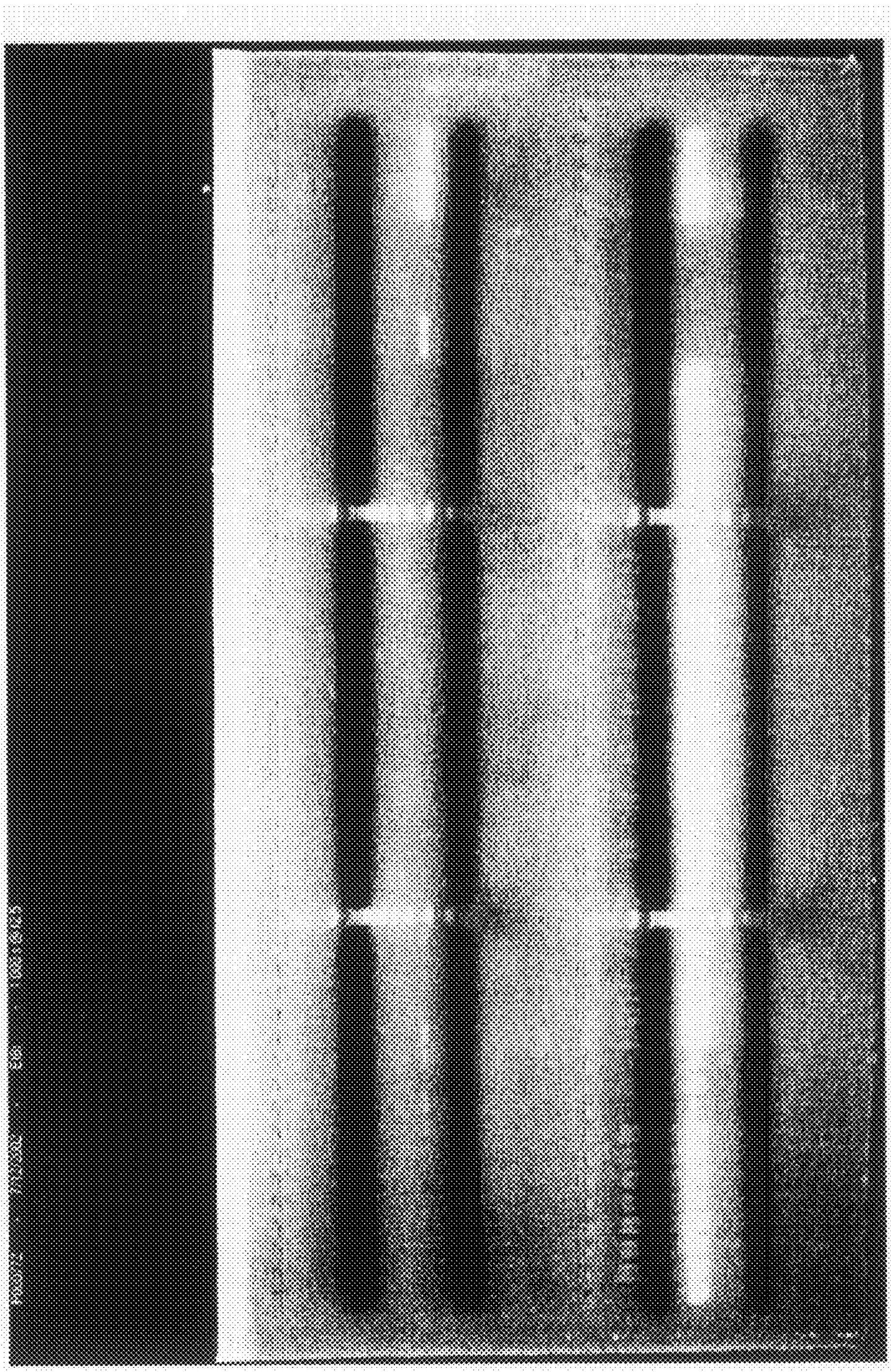

The seed in the bags listed below were each subjected to the seed wash protocol described in Example 2a, subjected to DNA extraction as described in Example 2b. PCR was conducted as described in Example 2c. The results are provided below. The results of the PCR and gel electrophoresis are provided in FIGS. 8*a*-8*c*.

Type of Seed: Watermelon. Number of seed per bag: 5,000.

| Batch# | Bag/Sample #s | Vol. PABST/Bag | Final Result |
|---|---|---|---|
| 539444 | 1 & 2 | 600 | Both Bags WEAK POS |
| 355992 | 3 & 4 | 600 | Both Bags WEAK POS |
| 539733 | 5 & 6 | 600 | Both Bags WEAK POS |
| 507080 | 7 & 8 | 600 | Both Bags Both Bags WEAK POS |
| 513097 | 9 & 10 | 600 | Both Bags NEG |
| 641699 | 11 & 12 | 600 | Both Bags NEG |
| 641699 | 13 & 14 | 600 | Both Bags NEG |
| 641696 | 15 & 16 | 600 | Both Bags NEG |

-continued

| | | | |
|---|---|---|---|
| 641696 | 17 & 18 | 600 | Both Bags NEG |
| Durango (298675)[1] | 19 & 20 | 600 | NEG (Bag 19) POS (Bag 20) |

NEG = NEGATIVE for Aac +200 mls extra
POS = POSITIVE for Aac
[1]Control (Commercially Available from Seminis Vegetable Seeds, Inc.)
Total PABST 6,200 mls

| PABST Buffer | Calls for | Amount weighed |
|---|---|---|
| Ascorbic acid (17.6 g/l) | 109.12 | 109.14 |
| Potassium Metabisulfite (2.2 g/l) | 13.64 | 13.64 |
| PH | 6.50 | 6.52 |

Optical Density @ 620 nm, Stock Aac suspension = 0.107
Colony Counts (48 hours):

| Sample # | $10^{-6}$ | $10^{-7}$ |
|---|---|---|
| 1 | 107 | 6 |
| 2 | 87 | 9 |
| 3 | 71 | 9 |
| 4 | 83 | 4 |
| 5 | 98 | 3 |
| 6 | 76 | 4 |
| 7 | 79 | 6 |
| 8 | 85 | 5 |
| Total | 686 | 46 |
| Average | 85.7 | 5.75 |

Stock population of Aac = (Average)(5)(*Countable dilution) = 986700 cfu
__3289______CFU/ml Seed wash
__4813______CFU/gram seed
Spike was made with 2.3 mls of the $10^{-3}$ dilution tube.
*The dilution rate which gave bacteria counts between 30 & 300.

Example 9

Testing of Commercial Seed Lots for the Presence of the Bacterium Aac

Figure 9C:
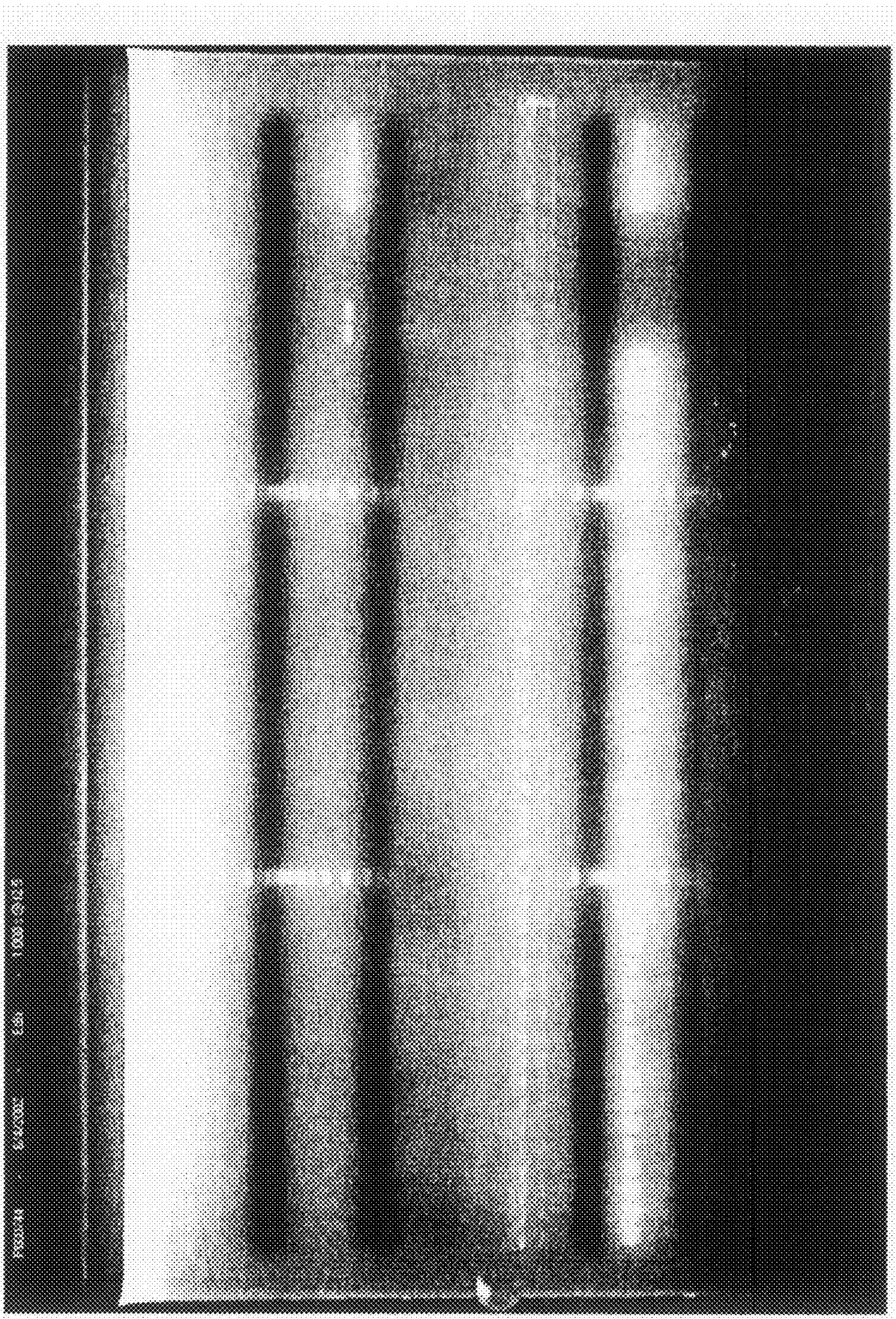

The seed in the bags listed below were each subjected to the seed wash protocol described in Example 2a, subjected to DNA extraction as described in Example 2b. PCR was conducted as described in Example 2c. The results are provided below. The results of the PCR and gel electrophoresis are provided in FIGS. 9*a*-9*c*.

Type of Seed: Watermelon. Number of seed per bag: 5,000.

| Batch# | Bag/Sample #s | Vol. PABST/Bag | Final Result |
|---|---|---|---|
| 634949 | 1 & 2 | 600 | Both Bags NEG |
| 610418 | 3 & 4 | 600 | Both Bags NEG |
| 610418 | 5 & 6 | 600 | Both Bags NEG |
| 501273 | 7 & 8 | 600 | Both Bags NEG |
| 501273 | 9 & 10 | 600 | Both Bags NEG |
| 636115 | 11 & 12 | 600 | Both Bags NEG |
| 610420 | 13 & 14 | 600 | Both Bags NEG |
| 610420 | 15 & 16 | 600 | Both Bags NEG |
| 583268 | 17 & 18 | 600 | Both Bags NEG |
| Sugar Baby[1] | 19 & 20 | 600 | NEG (Bag 19) POS (Bag 20) |

NEG = NEGATIVE for Aac +200 mls extra
POS = POSITIVE for Aac
[1]Control
Total PABST 6,200 mls -continued

| PABST Buffer | Calls for | Amount weighed |
|---|---|---|
| Ascorbic acid (17.6 g/l) | 109.12 | 109.12 |
| Potassium Metabisulfite (2.2 g/l) | 13.64 | 13.64 |
| PH | 6.50 | 6.51 |

Optical Density @ 620 nm, Stock Aac suspension = 0.102
Colony Counts (48 hours):

| Sample # | $10^{-6}$ | $10^{-7}$ |
|---|---|---|
| 1 | 81 | 9 |
| 2 | 107 | 6 |
| 3 | 91 | 5 |
| 4 | 110 | 11 |
| 5 | 79 | 6 |
| 6 | 74 | 7 |
| 7 | 86 | 6 |
| 8 | 113 | 7 |
| Total | 741 | 57 |
| Average | 92.6 | 7.1 |

Stock population of Aac = (Average)(5)(*Countable dilution) = 1064900 cfu
__3549______CFU/ml Seed wash
__5194______CFU/gram seed
Spike was made with 2.3 mls of the $10^{-3}$ dilution tube.
*The dilution rate which gave bacteria counts between 30 & 300.

Example 10

This Example provides a comparison of specificity of two different primer pairs (RST 90/91 and SEQ ID NOS: 1-2). Comparisons were made with isolates of *Acidovorax* spp. and numerous other bacterial isolates. All DNA was prepared using the 'boil prep' method which consists of making a suspension of the bacteria in 200 ul of water in a 1.5 ml Eppendorf tube and placing the tubes in a boiling water bath for about 10 minutes. Data is a compilation of two different experiments (PCR #71 and #169). ND=not done.

| | PCR response of two different primer sets | |
|---|---|---|
| Bacterial Isolate | RST 90/91 | SEQ ID NOS: 1-2 |
| *Pseudomonas syringae* pv. tomato A | – | – |
| *Pseudomonas syringae* pv. tomato B | – | – |
| *Pseudomonas syringae* pv. *lachrymans* A | – | – |
| *Pseudomonas syringae* pv. *lachrymans* B | – | – |
| *Clavibacter michiganensis* pv. *michiganensis* A | – | – |
| *Clavibacter michiganensis* pv. *michiganensis* B | – | – |
| *Xanthomonas campestris* pv. *vesicatoria* A | – | – |
| *Xanthomonas campestris* pv. *vesicatoria* B | – | – |
| *Acidovorax avenae* pv. *citrulli* 154-Indiana | 90 | 1 |
| *Acidovorax avenae* pv. *citrulli* 163-Guatemala | 0 | 0 |
| *Acidovorax avenae* pv. *citrulli* 107-Texas(citron) | ND | 0 |
| *Acidovorax avenae* pv. *citrulli* 170-Texas | ND | 0 |

-continued

| Bacterial Isolate | PCR response of two different primer sets RST 90/91 | SEQ ID NOS: 1-2 |
|---|---|---|
| *Acidovorax avenae* pv. *citrulli* 111-Georgia | ND | 0 |
| *Acidovorax avenae* pv. *citrulli* 12-S. Carolina | ND | 0 |
| *Acidovorax avenae* pv. *citrulli* 7500, New Zealand | ND | 0 |
| *Acidovorax avenae* pv. *citrulli* 37 D. Antibiotic Mut. | ND | 0 |
| *Acidovorax avenae* pv.*citrulli* 6 other isolates | ND | 6 |
| *Comomonas acidovorans* | 0 | – |
| *Xanthomonas campestris* pv. *carota* | ND | – |
| *Xanthomonas campestris* pv. *vitians* | ND | – |
| *Acidovorax avenae* pv. *avenae* | +[1] | 6 |
| *Acidovorax avenae* pv. *cattylae* | +[1] | 0 |
| *Acidovorax konjaci* | +[1] | 0 |
| *Acidovorax facilis* | –[1] | – |
| *Hydrenophaga* sp. "*H bacterium*" | –[1] | +(weak) |

[1]Indicates the response reported in ASRF grant reports from Stall and Kucarek, December 1994.

Example 11

In this example, four different sources of seed (2500 seed/sample) were grown in the greenhouse and evaluated for BFB to determine the percent transmission (% Trans). Different samples of the same seed sources (2500 seed/sample) were taken through the BFB seed assay and the final seed extract was separated into two samples. One sample was plated onto semiselective media (NBC) and the other was taken through the DNA extraction protocol (described in Example 1) and was subjected to PCR using two different primer sets. After two days of growth the NBC plates were sampled and subjected to PCR. Additional isolations were made to recover *Acidovorax*. The PCR response is expressed as positive (+) or negative (–). The intensity of the gel band on the positives is rated from low (+) to high (+++). All samples were tested undiluted and diluted 1:10.

| | | PCR responses | | | | | | | |
|---|---|---|---|---|---|---|---|---|---|
| | | RST 90/91 | | | | SEQ ID NOS: 1-2 | | | |
| | | Seedwash | | NBC | | Seedwash | | NBC | |
| Sample Label | % Trans. | $10^0$ | $10^{-1}$ | PCR | Isol. | $10^0$ | $10^{-1}$ | PCR | Isol. |
| "Low A" | 0.08 | – | + | – | – | + | +++ | – | – |
| "Low B" | 0.12 | ++ | ++ | – | – | +++ | +++ | – | – |
| "Hi B" | 8.34 | +++ | +++ | – | – | + | +++ | +*(faint)* | – |
| "Check" | 0.00 | – | – | – | – | – | – | – | – |

Example 12

This Example shows the effects of diluting the extracted DNA prior to running the material through a BioRad Sephadex column on the ability of the PCR to detect the presence of *Acidovorax avenae* pv *citrulli*. A dilution series (10 fold) was made from an original suspension of Aac that was 0.1 OD $620_{nm}$. Specific amounts were added to samples of 5,000 Charleston Grey watermelon seed. Further dilutions were plated onto Nutrient Agar and counts were made to determine the amount of cells added to the samples. Values are expressed as Colony Forming Units (CFU)/ml of seedwash suspension. Results are expressed as the number of positive PCR reactions over the total number of reactions.

PCR #208:

| Dilution factor prior to running a column | Number of Positive PCR Reactions over the total number of reactions at differing concentrations of Aac. 0 Cfu/ml | 1030 Cfu/ml | 5130 Cfu/ml | 25,700 Cfu/ml |
|---|---|---|---|---|
| Undiluted | 0/4 | 0/8 | 0/8 | 0/8 |
| 1:50 | 0/4 | 6/8 | 8/8 | 8/8 |
| 1:100 | 0/4 | 3/8 | 6/8 | 8/8 |

Example 13

This example provides a comparison of the sensitivity of two different primer pairs (RST 90/91 and SEQ ID NOS:1-2) in the detection of *Acidovorax* DNA from various sources at differing concentrations. Data is compiled from several different experiments.

| | | Lower limit of concentration of DNA yielding a positive PCR response | | |
|---|---|---|---|---|
| PCR # | DNA Source | RST 90/91 | SEQ ID NOS: 1-2 | Ratio RST/SEQ ID NOS: 1-2 |
| 56A | Culture boil prep | 0.8 ng | 0.2 ng | 5 |
| | Culture boil prep-older | 20.0 ng | 0.8 ng | 25 |
| | Purified DNA-culture | 160.0 pg | 6.4 pg | 25 |
| 57 | Purified Culture DNA | 3.2 pg | 0.02 pg | 125 |
| 59 | Purified Culture DNA | 400.0 pg | 0.6 pg | 625 |
| 70 | Purified Culture DNA | 20.0 pg | 2.0 pg | 10 |
| 73 | Purified Culture DNA | 100.0 pg | 10.0 pg | 10 |
| Range | | 3.2-800.0 pg | 0.03-160.0 pg | 5-625 |

Example 14

This Example provides a summary of several experiments showing the sensitivity of the PCR test in the detection of different concentrations of *Acidovorax avenae* pv *citrulli*. Samples of 5,000 watermelon seed were spiked with different amounts of bacteria. A dilution series (10 fold) was made from an original suspension of Aac that was 0.1 OD $620_{nm}$ and specific amounts were added to the seed samples. Further dilutions were plated onto Nutrient Agar and counts were made to determine the amount of cells added to the samples. Values are expressed as Colony Forming Units (CFU)/ml of seed-wash suspension. All experiments were done using the primers in SEQ ID NOS: 1-2 except Experiment 8 which included both RST 90/91 and the primers shown in SEQ ID NOS: 1-2. Results are expressed as the number of positive PCR reactions over the total number of PCR reactions run.

| Experiment 1 (PCR 247) | | Experiment 2 (PCR 252) | | Experiment 3 (PCR 261) | | Experiment 4 (PCR 267) | | Experiment 5 (PCR 268) | |
|---|---|---|---|---|---|---|---|---|---|
| CFU/ml | #Pos/tot | CFU/ml | #Pos/tot | CFU/ml | #Pos/tot | CFU/ml | #Pos/tot | CFU/ml | #Pos/tot |
| 0 | 0/6 | 0 | 0/4 | 0 | 0/4 | 0 | 0/4 | 0 | 0/4 |
| 624 | 12/12 | 25 | 5/8 | 159 | 8/8 | 301 | 8/8 | 191 | 8/8 |
| 1,293 | 12/12 | 123 | 8/8 | 616 | 8/8 | 904 | 8/8 | 574 | 8/8 |
| 3,879 | 12/12 | 247 | 8/8 | 1232 | 8/8 | 1804 | 6/6 | 1148 | 8/8 |

| Experiment 6 (PCR 275) | | Experiment 7 (PCR 355) | | Experiment 8-RST 90/91 primers (PCR 362) | | Experiment 8-SEQ ID NO: 1-2 (PCR 362) | |
|---|---|---|---|---|---|---|---|
| | | | | CFU/ml | CFU/ml | | |
| CFU/ml | #Pos/tot | CFU/ml | #Pos/tot | #Pos/tot | #Pos/tot | CFU/ml | #Pos/tot |
| 0 | 0/4 | 0 | 0/4 | 0 | 0/4 | 0 | 0/4 |
| 333 | 8/8 | 678 | 8/8 | 29 | 0/6 | 29 | 3/6 |
| 1000 | 8/8 | 1696 | 6/8 | 59 | 0/6 | 59 | 2/6 |
| 2000 | 8/8 | 3392 | 8/8 | 133 | 0/6 | 133 | 0/6 |
| | | | | 590 | 0/6 | 590 | 6/6 |

Example 15

This example demonstrates the detection of *Acidovorax avenae* subsp. *citrulli* in watermelon seed samples (5,000 seed/sample) spiked with naturally infected seed and broth cultures. One sample of each variety was spiked with ten (10) seed of a BFB naturally infected seedlot. A second sample was spiked with a specific volume of a bacterial suspension. A dilution series (10 fold) was made from an original suspension of Aac that was 0.1 OD $620_{nm}$. Specific amounts were added to samples of 5,000 seed and further dilutions were plated onto Nutrient Agar and counts were made to determine the amount of cells added to the samples. Values are expressed as Colony Forming Units (CFU)/ml of seed-wash suspension. The PCR response is expressed as positive (+) or negative (−). The intensity of the gel band on the positives is rated from low (+) to high (+++).

| | | | PCR Response | |
|---|---|---|---|---|
| Variety | Spike material | CFU/ml | RST 90/91 | SEQ ID NOS: 1-2 |
| Charleston Grey 133* | Single seed | — | +(faint) | ++ |
| " | Culture | 1,286 | − | + |
| Royal Charleston WR* | Single seed | — | + | +++ |
| " | Culture | 2,214 | − | ++ |
| Charlee* | Single seed | — | + | +++ |
| " | Culture | 1,185 | − | + |

-continued

| | | | PCR Response | |
|---|---|---|---|---|
| Variety | Spike material | CFU/ml | RST 90/91 | SEQ ID NOS: 1-2 |
| EH1952* | Single seed | — | + | +++ |
| " | Culture | 3,973 | − | + |
| Picnic* | Single seed | — | − | + |
| " | Culture | 2,392 | − | +(Very Faint) |

-continued

| Variety | Spike material | CFU/ml | PCR Response RST 90/91 | SEQ ID NOS: 1-2 |
|---|---|---|---|---|
| Sabrina* | Single seed | — | + | +++ |
| " | Culture | 3,570 | − | ++ |
| Starbrite* | Single seed | — | +(faint) | ++ |
| " | Culture | 1,392 | − | + |
| Sugarbrite* | Single seed | — | + | +++ |
| " | Culture | 3,164 | − | + |
| Sugar Baby* | Single seed | — | + | +++ |
| " | Culture | 3,131 | − | + |
| #Pos/Total | | | 8/18 | 18/18 |

*Commercially Available from Seminis Vegetable Seeds, Inc.

Example 16

This example provides a comparison of PCR versus grow-out test results in detection of *Acidovorax avenae* pv. *citrulli*. Thirty samples of 3300 watermelon seed each were obtained as blind samples. Half of the samples were grown the in greenhouse for 18 days and the other half were tested by the direct seed PCR assay. After all results were obtained the previous test result information was given. Results are expressed as the number of positive lots over the total number of lots tested.

PCR #757:

| Test Method | # seedlots positive for Aac/total number tested (Each column heading represents the previous three test results obtained for the samples) +++ | −++ | −−− |
|---|---|---|---|
| GH Growout | 5/5 | 4/5 | 0/5 |
| PCR Seed assay | 5/5 | 3/5[1] | 0/5 |

[1]All five of the samples yielded unusual DNA pellets; the pellets would not resuspend into solution. After physically breaking up the pellets, three samples were found positive in the PCR test. The other two samples were spiked with known Aac DNA and run in the PCR. The test was positive indicating that no inhibitor was present. This also suggests that the DNA was bound by the pellet and rendered unavailable for a PCR reaction to occur.

Example 17

Example 17 provides a comparison of PCR versus grow-out test results in detection of *Acidovorax avenae* pv. *citrulli* in watermelon seed. Individual seed of a known naturally infected seed lot were planted in pots or flats and grown out under greenhouse conditions conducive for disease expression. All pots and flats were monitored daily for disease symptoms and any plants showing symptoms were confirmed by plant tissue PCR. In addition, single seeds of the same source were added to samples of 5,000 known healthy watermelon seed and run through the direct seed PCR assay. Results are expressed as the percent of BFB in the samples.

| Test Method | Percent Germination (Infected seed source) | Percent BFB (#Pos/Total) |
|---|---|---|
| GH Growout: | | |
| Expt 1-1 infected watermelon seed/pot, pots covered with plastic bags, area covered with shade cloth. | 96.4 | 30.3 (73/241) |
| - 1 infected watermelon seed/pot, pots uncovered, and normal greenhouse conditions. | 92.8 | 18.5 (43/232) |
| Expt 2-1 infected watermelon seed per pot, pots uncovered, and normal greenhouse conditions. | 93.6 | 9.4 (22/234) |
| Expt 3-One infected watermelon seed per flat with 200 healthy seed, normal greenhouse conditions. | 95.0 | 8.4 (20/237) |
| PCR direct seed assay: | | |
| Expt 1-1 infected watermelon seed in 5,000 healthy seed of Sugar Baby. | -NA- | 100 (16/16) |
| Expt 2-One infected watermelon seed in 5,000 healthy seed of Charleston Gray. | -NA- | 100 (16/16) |

All references referred to herein are hereby incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made to the composition, operation, and arrangement of the method of the present invention described herein without departing from the concept and scope of the invention as defined in the following claims.

What is claimed is:

1. A method of detecting the presence of *Acidovorax avenae* subsp. *citrulli* in a test sample, the method comprising the steps of:

(a) providing DNA from a test sample suspected of containing DNA of *Acidovorax avenae* subsp. *citrulli;*

(b) amplifying a selected target sequence from said test sample using a pair of oligonucleotide primers under amplification conditions to produce an amplification product, wherein said selected target sequence is SEQ ID NO: 3, or wherein each of said pair of oligonucleotide primers consists of 15-25 contiguous nucleotides of SEQ ID NO:3, or the complement thereof; and (c) detecting the presence of said amplification product produced in step (b) as an indication of the presence of *Acidovorax avenae* subsp. *citrulli* in the test sample.

2. A method of evaluating or monitoring the efficacy of a treatment utilized to eliminate *Acidovorax avenae* subsp. *citrulli*, the method comprising the steps of:

(a) providing a first test sample suspected of containing DNA of *Acidovorax avenae* subsp. *citrulli;*

(b) providing a first DNA from said first test sample;

(c) amplifying a sequence of said first DNA of step (b) using a pair of oligonucleotide primers to amplify a selected target sequence under amplification conditions to produce a first amplification product, wherein said selected target sequence is SEQ ID NO: 3, or wherein each of said pair of oligonucleotide primers consists of 15-25 contiguous nucleotides of SEQ ID NO:3 or the complement thereof;

(d) detecting the presence of said first amplification product produced in step (c) as an indication of the presence of *Acidovorax avenae* subsp. *citrulli* in the first test sample;

(e) treating said first test sample, or a portion thereof, with a composition to reduce or eradicate *Acidovorax avenae* subsp. *citrulli*, thereby producing a treated sample;

(f) providing a second test sample from said treated sample, or treated portion thereof;

(g) providing a second DNA from said second test sample;

(h) amplifying a sequence in said second DNA using said pair of oligonucleotide primers under amplification conditions to produce a second amplification product;

(i) detecting the presence of said second amplification product produced in step (h) as an indication of the presence of *Acidovorax avenae* subsp. *citrulli* in said second test sample; and (j) comparing the amount of said second amplification product or absence of said second amplification product in said second test sample to the amount of said first amplification product detected in said first test sample in step (d) as an indication of whether said treating step (e) has reduced or eradicated *Acidovorax avenae* subsp. *citrulli* in said treated sample.

3. A test kit for identifying the presence of *Acidovorax avenae* subsp. *citrulli*, comprising: a pair of oligonucleotide primers to amplify a selected target sequence under amplification conditions, wherein said selected target sequence is SEQ ID NO: 3, and wherein each of said pair of oligonucleotide primers consists of 15-25 contiguous nucleotides of SEQ ID NO:3 or the complement thereof.

4. A method of treating a sample to reduce or eradicate *Acidovorax avenae* subsp. *citrulli*, the method comprising the steps of:

(a) providing a first test sample suspected of containing DNA of *Acidovorax avenae* subsp. *citrulli;*

(b) providing DNA from said first test sample;

(c) amplifying a sequence of the DNA of step (b) using a pair of oligonucleotide primers to amplify a selected target sequence under amplification conditions to produce an amplification product, wherein said selected target sequence is SEQ ID NO: 3 or wherein each of said pair of oligonucleotide primers consists of 15-25 contiguous nucleotides of SEQ ID NO:3 or the complement thereof;

(d) detecting the presence of said amplification product produced in step (c) as an indication of the presence of *Acidovorax avenae* subsp. *citrulli* in said first test sample; and (e) treating said sample, or a portion thereof, with a composition to reduce or eradicate *Acidovorax avenae* subsp. *citrulli*.

5. The method of claim 1, wherein said test sample is a seed lot.

6. The method of claim 1, wherein said test sample is a sample of bacterial cells or microorganisms suspected of containing DNA of *Acidovorax avenae* subsp. *Citrulli*.

7. The method of claim 2, wherein said first test sample is obtained from a seed lot.

8. The method of claim 2, wherein said first test sample is obtained from cells or microorganisms suspected of containing *Acidovorax avenae* subsp. *citrulli*.

9. The method of claim 4, wherein said first test sample is obtained from a seed lot.

10. The method of claim 4, wherein said first test sample is obtained from cells or microorganisms suspected of containing *Acidovorax avenae* subsp. *citrulli*.

11. The method of claim 1, wherein said amplifying further employs a polynucleotide probe for detection of said amplification product.

12. The method of claim 2, wherein said amplifying further employs cm a polynucleotide probe for detection of said first amplification product.

13. The method of claim 2, wherein said amplifying further employs a polynucleotide probe for detection of said second amplification product.

14. The kit of claim 3, further comprising a polynucleotide probe for detection of said selected target sequence.

15. The method of claim 4, wherein said amplifying further employs a polynucleotide probe for detection of said amplification product.

16. A method of detecting the presence of *Acidovorax avenae* subsp. *citrulli* in a test sample, the method comprising the steps of:

(a) providing DNA from a test sample suspected of containing DNA of *Acidovorax avenae* subsp. *citrulli;*

(b) amplifying a selected target sequence from said test sample using a pair of oligonucleotide primers under amplification conditions to produce an amplification product, wherein said selected target sequence is SEQ ID NO: 3 and each of said pair of oligonucleotide primers consists of 15-25 contiguous nucleotides of SEQ ID NO:3 or the complement thereof; and (c) detecting the presence of said amplification product produced in step (b) as an indication of the presence of *Acidovorax avenae* subsp. *citrulli* in the test sample.

17. The method of claim 16, wherein said test sample is a seed lot.

18. The method of claim 16, wherein said test sample is a sample of bacterial cells or microorganisms suspected of containing DNA of *Acidovorax avenae* subsp. *Citrulli*.

19. The method of claim 16, wherein said amplifying further employs a polynucleotide probe for detection of said amplification product.

20. A method of evaluating or monitoring the efficacy of a treatment utilized to eliminate *Acidovorax avenae* subsp. *citrulli*, the method comprising the steps of (a) providing a first test sample suspected of containing DNA of *Acidovorax avenae* subsp. *citrulli;*

(b) providing a first DNA from said first test sample;

(c) amplifying a sequence of said first DNA of step (b) using a pair of oligonucleotide primers to amplify a selected target sequence under amplification conditions to produce a first amplification product, wherein said selected target sequence is SEQ ID NO: 3 and each of said pair of oligonucleotide primers consists of 15-25 contiguous nucleotides of SEQ ID NO:3 or the complement thereof;

(d) detecting the presence of said first amplification product produced in step (c) as an indication of the presence of *Acidovorax avenae* subsp. *citrulli* in the first test sample;

(e) treating said first test sample, or a portion thereof, with a composition to reduce or eradicate *Acidovorax avenae* subsp. *citrulli*, thereby producing a treated sample;

(f) providing a second test sample from said treated sample, or treated portion thereof;

(g) providing a second DNA from said second test sample;

(h) amplifying a sequence in said second DNA using said pair of oligonucleotide primers under amplification conditions to produce a second amplification product;

(i) detecting the presence of said second amplification product produced in step (h) as an indication of the presence of *Acidovorax avenae* subsp. *citrulli* in said second test sample; and (j) comparing the amount of said second amplification product or absence of said second amplification product in said second test sample to the amount of said first amplification product detected in said first test sample in step (d) as an indication of whether said treating step (e) has reduced or eradicated *Acidovorax avenae* subsp. *citrulli* in said treated sample.

21. The method of claim 20, wherein said first test sample is obtained from a seed lot.

22. The method of claim 20, wherein said first test sample is obtained from cells or microorganisms suspected of containing *Acidovorax avenae* subsp. *citrulli*.

23. The method of claim 20, wherein said amplifying further employs a polynucleotide probe for detection of said first amplification product.

24. The method of claim 20, wherein said amplifying further employs a polynucleotide probe for detection of said second amplification product.

25. A method of treating a sample to reduce or eradicate *Acidovorax avenae* subsp. *citrulli*, the method comprising the steps of:

(a) providing a first test sample suspected of containing DNA of *Acidovorax avenae* subsp. *citrulli;*

(b) providing DNA from said first test sample;

(c) amplifying a sequence of the DNA of step (b) using a pair of oligonucleotide primers to amplify a selected target sequence under amplification conditions to produce an amplification product, wherein said selected target sequence is SEQ ID NO: 3 and each of said pair of oligonucleotide primers consists of 15-25 contiguous nucleotides of SEQ ID NO:3 or the complement thereat (d) detecting the presence of said amplification product produced in step (c) as an indication of the presence of *Acidovorax avenae* subsp. *citrulli* in said first test sample; and (e) treating said sample, or a portion thereof, with a composition to reduce or eradicate *Acidovorax avenae* subsp. *citrulli*.

26. The method of claim 25, wherein said first test sample is obtained from a seed lot.

27. The method of claim 25, wherein said first test sample is obtained from cells or microorganisms suspected of containing *Acidovorax avenae* subsp. *citrulli*.

28. The method of claim 25, wherein said amplifying further employs a polynucleotide probe for detection of said selected target sequence.

* * * * *

SEQUENCE LISTING

```
<160> NUMBER OF SEQ ID NOS: 3

<210> SEQ ID NO 1
<211> LENGTH: 18
<212> TYPE: DNA
<213> ORGANISM: Acidovorax avenae subsp. citrulli

<400> SEQUENCE: 1

cgcgccgacc gagacctg                                                    18
```

-continued

```
<210> SEQ ID NO 2
<211> LENGTH: 18
<212> TYPE: DNA
<213> ORGANISM: Acidovorax avenae subsp. citrulli

<400> SEQUENCE: 2

ggggcacgcc aacatcct                                              18


<210> SEQ ID NO 3
<211> LENGTH: 392
<212> TYPE: DNA
<213> ORGANISM: Acidovorax avenae subsp. citrulli

<400> SEQUENCE: 3

acatggccac ggcgatgagg atgcccggcg cgaagccggc gatgaagagc gcgccgaccg    60

agacctgctc gtcctgcagc gcgtagatga tcatgatgat cgagggcggg atgatgggcc   120

ccacgatggc cgtgctggcg gtgagcgcgg cggcgtatgc gcgcgagtag cccgccttgt   180

ccatcatctt gaccatcatc gagccgggcc ccgccgcgtc ggccagggcc gagcccgaga   240

tgcccgagaa cagcgtgagc gacaggatgt tggcgtgccc caggcccccg cgcaggtggc   300

ccacgaactg cgcggcgaag cgcagcagca ccacggtgag cgcgccgccg gacatgatct   360

cggccgcgag gatgaagaag gcacggccat cg                                392
```